Figure 1:
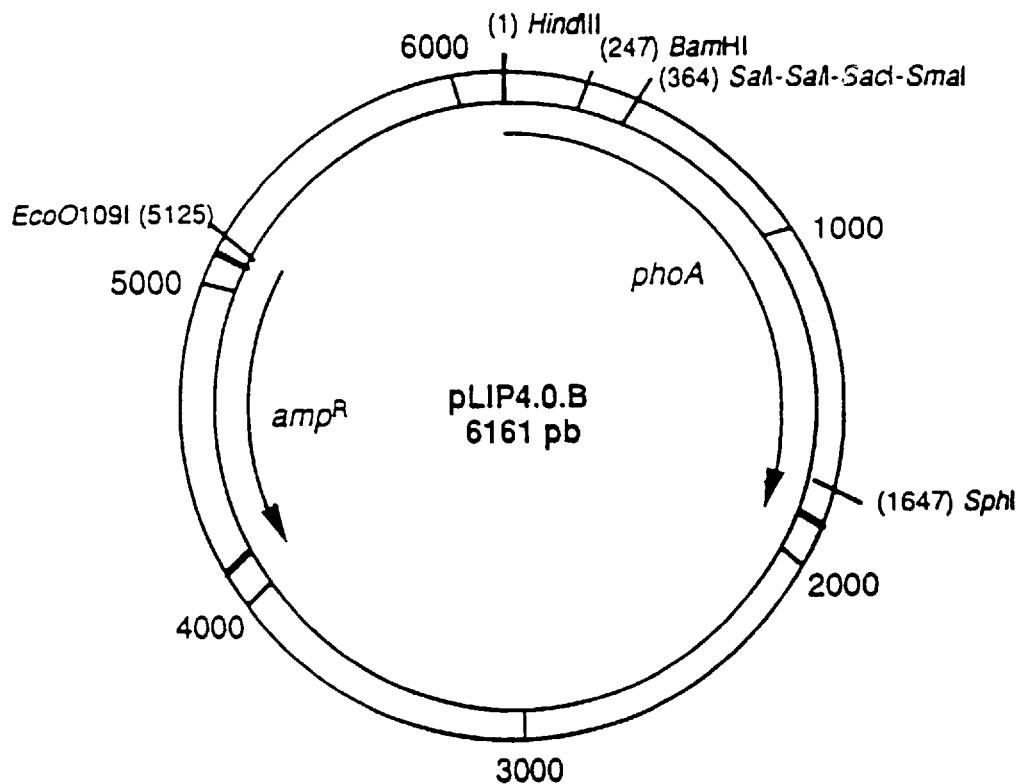

United States Patent [19]
Boulain et al.

[11] Patent Number: 5,891,699
[45] Date of Patent: Apr. 6, 1999

[54] MODIFIED BACTERIAL ALKALINE PHOSPHATASES AND THEIR APPLICATIONS

[75] Inventors: Jean-Claude Boulain, Palaiseau; Laurence Cattolico, Sceaux; Frédéric Ducancel, Longjumeau; André Menez, Magny les Hameaux, all of France

[73] Assignee: Commissariat a l'Energie Atomique, Paris, France

[21] Appl. No.: 673,312

[22] Filed: Jun. 28, 1996

[30] Foreign Application Priority Data

Jun. 29, 1995 [FR] France ................................. 95 07833

[51] Int. Cl.⁶ .............................. C12N 9/14; C12N 15/00; C12N 1/20; C12P 21/06
[52] U.S. Cl. .................. 435/195; 435/172.1; 435/172.3; 435/69.1; 435/252.3; 435/320.1; 435/849; 536/23.1; 536/23.7
[58] Field of Search ................................ 435/7.6, 21, 68, 435/69.1, 89, 92, 252.3, 320.1, 195, 172.1, 172.3; 536/23.1, 23.7

[56] References Cited

U.S. PATENT DOCUMENTS 5,362,644  11/1994  Boquet et al. ..................... 435/252.3
5,534,223   7/1996  Boquet et al. ..................... 422/61

FOREIGN PATENT DOCUMENTS

WO 94/01531  1/1994  WIPO.

OTHER PUBLICATIONS

Claude M.L. Janeway et al., "Magnesium in the Active Site of *Escherichia coli* Alkaline Phosphatase is Important for Both Structural Stabilization and Catalysis", Biochemistry, vol. 32, pp. 160–1609, 1993.

Daniel Gillet et al., Insertion of a Disulfide–Containing Neurotoxin into *E. coli* Alkaline Phosphatase: The Hybrid Retains Both Biological Activities, Protein Engineering, vol. 5, No. 3, pp. 273–278, 1992.

J.E. Murphy et al., "Why are Mammalian Alkaline Phosphatase Much More Active than Bacterial Alkaline Phosphatases", Molecular Microbiology, vol. 12, No. 3, 1994.

Janeway et al. (1993) Biochemistry, 32:1601–1609, Feb. 16, 1993.

Anal. Chem, (1993), vol. 55, pp. 1779–1784, "Enzyme Immunoassay Using a Rat Prolactin–Alkaline Phosphatase Recombinant Tracer", Daniel Gillet, et al.

Journal of Immunological Methods, vol. 169, 1994, pp. 205–211, "Recombinant Technology in the Preparation of Immunogen and Enzymatic Tracer. Application to the Development of an Enzyme Immunoassay for Rat Prolactin", Eric Ezan, et al.

Journal of Immunological Methods, vol. 181, 1995, pp. 177–186, "Recombinant Antibody–Alkaline Phosphatase Conjugates for Diagnosis of Human IgGs: Application to Anti–HBsAg Detection", Alice Carrier, et al.

Protein Engineering, vol. 5, No. 3, pp. 273–278, 1992, "Insertion of a Disulfide–Containing Neurotoxin into *E. coli* Alkaline Phosphatase: The Hybrid Retains both Biological Activities", Daniel Gillet, et al.

Bio/Technology, vol. 11, May 1993, pp. 601–605, Recombinant Colorimetric Antibodies: Construction and Characterization of a Bifunctional F(ab)2/Alkaline Phosphatase Conjugate Produced in *Escherichia coli*, Frederic Ducancel, et al.

*Primary Examiner*—Robert A. Wax
*Assistant Examiner*—Tekchand Saidha
*Attorney, Agent, or Firm*—Oblon, Spivak, McClelland, Maier & Neustadt, P.C.

[57] ABSTRACT

Modified alkaline phosphatases of bacterial origin (BAP or bacterial alkaline phosphatase) which consist of a bacterial alkaline phosphatase sequence in which at least one of the amino acid residues in position 329 or in position 330 is replaced by another amino acid residue, which modified bacterial alkaline phosphatases exhibit both significantly improved enzymic properties and an increased thermal stability, and their applications, in particular in immunoenzymic assays (reagents and diagnostic kits).

Method for selecting mutants of alkaline phosphatases which possess significantly improved enzymic properties.

18 Claims, 10 Drawing Sheets

AAGCTTTGGAGATTATCGTCACTGCAATGCTTCGCAATATGGCGCAAAATGACCAACAGCGGTTGATTGATCAGGT

AGAGGGGGCGCTGTACGAGGTAAAGCCCGATGCCAGCATTCCTGACGACGATACGGAGCTGCTGCGCGATTACGTA

AAGAAGTTATTGAAGCATCCTCGTCAGTAAAAAGTTAATCTTTTCAACAGCTGTCATAAAGTTGTCACGGCCGAGA

CTTATAGTCGCTTTGTTTGGATCCTTTAATGTATTTGTACATGGAGAAAATAAAGTGAAACAAAGCACTATTG

CACTGGCACTCTTACCGTTACTGTTTACCCCTGTGACAAAAGCCCGGACACCAGAAATGCCC<u>GTCGA</u>

<u>CTTCAGTCGACGAGCTCCCGGG</u>GTTCTGGAAAACCGGGCTGCTCAGGGCGATATTACTGCACCCGGC

GGTGCTCGCCGTTTAACGGGTGATCAGACTGCCGCTCTGCGTGATTCTCTTAGCGATAAACCTGCAA

AAAATATTATTTTGCTGATTGGCGATGGGATGGGGGACTCGGAAATTACTGCCGCACGTAATTATGC

CGAAGGTGCGGGCGGCTTTTTTAAAGGTATAGATGCCTTACCGCTTACCGGGCAATACACTCACTAT

GCGCTGAATAAAAAAACCGGCAAACCGGACTACGTCACCGACTCGGCTGCATCAGCAACCGCCTGGT

CAACCGGTGTCAAAACCTATAACGGCGCGCTGGGCGTCGATATTCACGAAAAAGATCACCCAACGAT

TCTGGAAATGGCAAAAGCCGCAGGTCTGGCGACCGGTAACGTTTCTACCGCAGAGTTGCAGGATGCC

ACGCCCGCTGCGCTGGTGGCACATGTGACCTCGCGCAAATGCTACGGTCCGAGCGCGACCAGTGAAA

AATGTCCGGGTAACGCTCTGGAAAAAGGCGGAAAAGGATCGATTACCGAACAGCTGCTTAACGCTCG

TGCCGACGTTACGCTTGGCGGCGGCGCAAAAACCTTTGCTGAAACGGCAACCGCTGGTGAATGGCAG

GGAAAAACGCTGCGTGAACAGGCACAGGCGCGTGGTTATCAGTTGGTGAGCGATGCTGCCTCACTGA

ATTCGGTGACGGAAGCGAATCAGCAAAAACCCCTGCTTGGCCTGTTTGCTGACGGCAATATGCCAGT

GCGCTGGCTAGGACCGAAAGCAACGTACCATGGCAATATCGATAAGCCCGCAGTCACCTGTACGCCA

AATCCGCAACGTAATGACAGTGTACCAACCCTGGCGCAGATGACCGACAAAGCCATTGAATTGTTGA

GTAAAAATGAGAAAGGCTTTTTCCTGCAAGTTGAAGGTGCGTCAATCGATAAACAGGATCATGCTGC

*FIG. 2A*

```
GAATCCTTGTGGGCAAATTGGCGAGACGGTCGATCTCGATGAAGCCGTACAACGGGCGCTGGAATTC

GCTAAAAAGGAGGGTAACACGCTGGTCATAGTCACCGCTGATCACGCCCACGCCAGCCAGATTGTTG

CGCCGGATACCAAAGCTCCGGGCCTCACCCAGGCGCTAAATACCAAAGATGGCGCAGTGATGGTGAT

GAGTTACGGGAACTCCGAAGAGGATTCACAAGAACATACCGGCAGTCAGTTGCGTATTGCGGCGTAT

GGCCCGCATGCCGCCAATGTTGTTGGACTGACCGACCAGACCGATCTCTTCTACACCATGAAAGCCG

CTCTGGGGCTGAAATAA AACCGCGCCCGGCAGTGAATTTTCGCTGCCGGGTGGTTTTTTTGCTGTTAGCAACCA

GACTTAATGGCAGATCACGGGCGCATACGCTCATGGTTAAAACATGAAGAGGGATGGTGCTATGAAAATAACATTA

CTGGTTACCTTGCTTTTCGGTCTGGTTTTTTTAACCACCGTCGGCGCTGCCGAGAGAACTTTAACCCCACAACAAC

AGCGTATGACCTCCTGTAATCAGCAGGCGACGGCGCAGGCGTTGAAAGGGGATGCTCGTAAGACCTACATGAGTGA

TTGCCTGAAGAACAGCAAGTCTGCGCCTGGCGAAAAAAGTTTGACGCCACAGCAGCAAAAGATGCGCGAATGCAAT

AATCAAGCAACACAACAATCTCTGAAAGGTGATGATCGTAATAAGTTTATGAGTGCCTGCCTCAAGAAAGCCGCCT

GATACCTGATAGTGCTAACGGGTGAGCTACGAAAATGGCTCACCCGAAATATCATACTTCTGCCTTTAGCTCCGTC

TCTATAATTTGGGAAAATTGTTTCTGAATGTTCCCAAAAATAATGAATGATGAAAACTTTTTCAAAAAAGCGGCGG

CGCACGGGGAGGAACCTCCTTTAACTCCTCAAAACGAACATCAGCGGTCCGGGCTGCGCTTCGCCCGTCGCGTCAG

ACTACCCCGTGCGGTTGGCCTGGCTGGCATGTTCTTACCGATTGCTTCAACGCTGGTTTCACACCCGCCGCCGGGC

TGGTGGTGGCTGGTGTTGGTCGGCTGGGCGTTCGTCTGGCCGCATTTAGCCTGGCAGATAGCGAGCAGGGCCGTCG

ATCCGCTTAGCCGGGAAATTTACAACTTAAAAACCGATGCAGTATTAGCGGGAATGTGGGTAGGCGTAATGGGCGT

AAACGTGCTGCCTTCCACCGCGATGTTGATGATTATGTGTCTGAATTTGATGGGGGCAGGCGGCCCCCGTCTGTTT

GTCGCGGGTCTGGTGTTGATGGTGGTTTCCTGCCTTGTCACCCTCGAGCAAGACGTTTCCCGTTGAATATGGCTCA

TAACACCCCTTGTATTACTGTTTATGTAAGCAGACAGTTTTATTGTTCATGATGATATATTTTTATCTTGTGCAAT
```

FIG. 2B

```
GTAACATCAGAGATTTTGAGACACAACGTGGCTTTGTTGAATAAATCGAACTTTTGCTGAGTTGAAGGATCAGATC

ACGCATCTTCCCGACAACGCAGACCGTTCCGTGGCAAAGCAAAAGTTCAAAATCACCAACTGGTCCACCTACAACA

AAGCTCTCATCAACCGTGGCTCCCTCACTTTCTGGCTGGATGATGGGGCGATTCAGGCCTGGTATGAGTCAGCAAC

ACCTTCTTCACGAGGCAGACCTCAGCGCTAGCGGAGTGTATACTGGCTTACTATGTTGGCACTGATGAGGGTGTCA

GTGAAGTGCTTCATGTGGCAGGAGAAAAAAGGCTGCACCGGTGCGTCAGCAGAATATGTGATACAGGATATATTCC

GCTTCCTCGCTCACTGACTCGCTACGCTCGGTCGTTCGACTGCGGCGAGCGGAAATGGCTTACGAACGGGGCGGAG

ATTTCCTGGAAGATGCCAGGAAGATACTTAACAGGGAAGTGAGAGGGCCGCGGCAAAGCCGTTTTTCCATAGGCTC

CGCCCCCTGACAAGCATCACGAAATCTGACGCTCAAATCAGTGGTGGCGAAACCCGACAGGACTATAAAGATACC

AGGCGTTTCCCCCTGGCGGCTCCCTCGTGCGCTCTCCTGTTCCTGCCTTTCGGTTTACCGGTGTCATTCCGCTGTT

ATGGCCGCGTTTGTCTCATTCCACGCCTGACACTCAGTTCCGGGTAGGCAGTTCGCTCCAAGCTGGACTGTATGCA

ATGGCCGCGTTTGTCTCATTCCACGCCTGACACTCAGTTCCGGGTAGGCAGTTCGCTCCAAGCTGGACTGTATGCA

CGAACCCCCCGTTCAGTCCGACCGCTGCGCCTTATCCGGTAACTATCGTCTTGAGTCCAACCCGGAAAGACATGCA

AAAGCACCACTGGCAGCAGCCACTGGTAATTGATTTAGAGGAGTTAGTCTTGAAGTCATGCGCCGGTTAAGGCTAA

ACTGAAAGGACAAGTTTTGGTGACTGCGCTCCTCCAAGCCAGTTACCTCGGTTCAAAGAGTTGGTAGCTCAGAGAA

CCTTCGAAAAACCGCCCTGCAAGGCGGTTTTTTCGTTTTCAGAGCAAGAGATTACGCGCAGACCAAAACGATCTCA

AGAAGATCATCTTATTAAGGGGTCTGACGCTCAGTGGAACGAAAACTCACGTTAAGGGATTTTGGTCATGAGATTA

TCAAAAAGGATCTTCACCTAGATCCTTTTAAATTAAAAATGAAGTTTTAAATCAATCTAAAGTATATATGAGTAAA

CTTGGTCTGACAGTTACCAATGCTTAATCAGTGAGGCACCTATCTCAGCGATCTGTCTATTTCGTTCATCCATAGT

TGCCTGACTCCCCGTCGTGTAGATAACTACGATACGGGAGGGCTTACCATCTGGCCCCAGTGCTGCAATGATACCG

CGAGACCCACGCTCACCGGCTCCAGATTTATCAGCAATAAACCAGCCAGCCGGAAGGGCCGAGCGCAGAAGTGGTC
```

*FIG. 2C*

CTGCAACTTTATCCGCCTCCATCCAGTCTATTAATTGTTGCCGGGAAGCTAGAGTAAGTAGTTCGCCAGTTAATAG

TTTGCGCAACGTTGTTGCCATTGCTGCAGGCATCGTGGTGTCACGCTCGTCGTTTGGTATGGCTTCATTCAGCTCC

GGTTCCCAACGATCAAGGCGAGTTACATGATCCCCCATGTTGTGCAAAAAAGCGGTTAGCTCCTTCGGTCCTCCGA

TCGTTGTCAGAAGTAAGTTGGCCGCAGTGTTATCACTCATGGTTATGGCAGCACTGCATAATTCTCTTACTGTCAT

GCCATCCGTAAGATGCTTTTCTGTGACTGGTGAGTACTCAACCAAGTCATTCTGAGAATAGTGTATGCGGCGACCG

AGTTGCTCTTGCCCGGCGTCAACACGGGATAATACCGCGCCACATAGCAGAACTTTAAAAGTGCTCATCATTGGAA

AACGTTCTTCGGGGCGAAAACTCTCAAGGATCTTACCGCTGTTGAGATCCAGTTCGATGTAACCCACTCGTGCACC

CAACTGATCTTCAGCATCTTTTACTTTCACCAGCGTTTCTGGGTGAGCAAAAACAGGAAGGCAAAATGCCGCAAAA

AAGGGAATAAGGGCGACACGGAAATGTTGAATACTCATACTCTTCCTTTTTCAATATTATTGAAGCATTTATCAGG

GTTATTGTCTCATGAGCGGATACATATTTGAATGTATTTAGAAAAATAAACAAATAGGGGTTCCGCGCACATTTCC

CCGAAAAGTGCCACCTGACGTCTAAGAAACCATTATTATCATGACATTAACCTATAAAAATAGGCGTATGCACGAG

CCGAAAAGTGCCACCTGACGTCTAAGAAACCATTATTATCATGACATTAACCTATAAAAATAGGCGTATGCACGAG

GCCCTTTCGTCTTCAAGAATTTTATAAACCGTGGAGCGGGCAATACTGAGCTGATGAGCAATTTCCGTTGCACCAG

TGCCCTTCTGATGAAGCGTCAGCACGACGTTCCTGTCCACGGTACGCCTGCGGCCAAATTTGATTCCTTTCAGCTT

TGCTTCCTGTCGGCCCTCATTCGTGCGCTCTAGGATCCTCCGGCGTTCAGCCTGTGCCACAGCCGACAGGATGGTG

ACCACCATTTGCCCCATATCACCGTCGGTACTGATCCCGTCGTCAATAAACCGAACCGCTACACCCTGAGCATCAA

ACTCTTTTATCAGTTGGATCATGTCGGCGTGTCGCGGCCAAGACGGTCGAGCTTCTTCACCAGAATGACATCACCT

TCCTCCACCTTCATCCTCAGCAAATCCAGCCCTTCCCGATCTGTTGAACTGCCGGATGCCTTGTCGGTAAAGATGC

GGTTAGCTTTTACCCCTGCATCTTTGAGCGCTGAGGTCTGCCTCGTGAAGAAGGTGTTGCTGACTCATACCAGGCC

TGAATCGCCCCATCATCCAGCCAGAAAGTGAGGGAGCCACGGTTGATGAGAGCTTTGTTGTAGGTGGACCAGTTGG

TGATTTTGAACTTTTGCTTTGCCACGGAACGGTCTGCGTTGTCGGGAAGATGCGTGATCTGATCCTTCAATCAGC

*FIG. 2D*

AAAAGTTCGATTTATTCAACAAAGCCGCCGTCCCGTCAAGTCAGCGTAATGCTCTGCCAGTGTTACAACCAATTAA

CCAATTCTGATTAGAAAAACTCATCGAGCATCAAATGAAACTGCAATTTATTCATATCAGGATTATCAATACCATA

TTTTTGAAAAAGCCGTTTCTGTAATGAAGGAGAAAACTCACCGAGGCAGTTCCATAGGATGGCAAGATCCTGGTAT

CGGTCTGCGATTCCGACTCGTCCAACATCAATACAACCTATTAATTTCCCCTCGTCAAAAATAAGGTTATCAAGTG

AGAAATCACCATGAGTGACGACTGAATCCGGTGAGAATGGCAATTCG

*FIG. 2E* tcgacttcgttaaccagcacctgtgcgggtcccacctggtggaagctttgtatctggtgtgcggcgagcgtggctt
gaagcaattggtcgtggacacgcccagggtggaccaccttcgaaacatagaccacacgccgctcgcaccgaa cttctacaccccgaagacgcgtcgtgaagcggaagatctgcaagtgggccaggtggaactgggcgggggg
gaagatgtggggcttctgcgcagcacttcgccttctagacgttcacccggtccaccttgacccgccccc cccgggcgccggcagcctgcaaccgctggcgctggagggcagcctccagaagcgtggcattgtggagc
gggcccgcggccgtcggacgttggcgaccgcgacctcccgtcggaggtcttcgcaccgtaacacctcg agtgttgtactagtatctgcagcctgtaccagctggagaattactgcaacggagct
tcacaacatgatcatagacgtcggacatggtcgacctcttaatgacgttgcc

*FIG. 6*

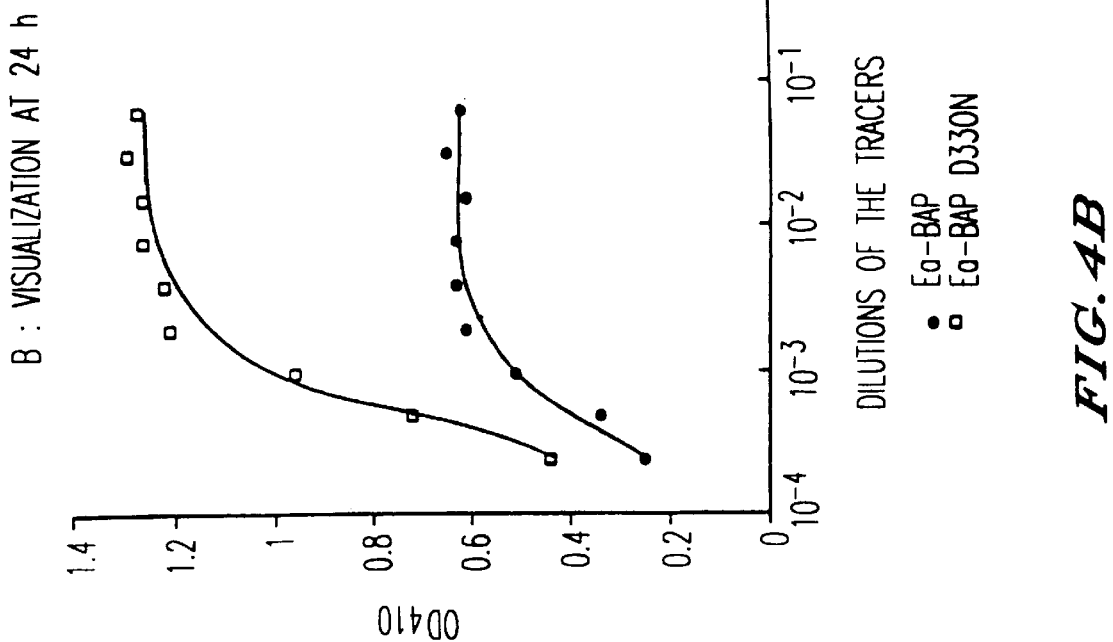
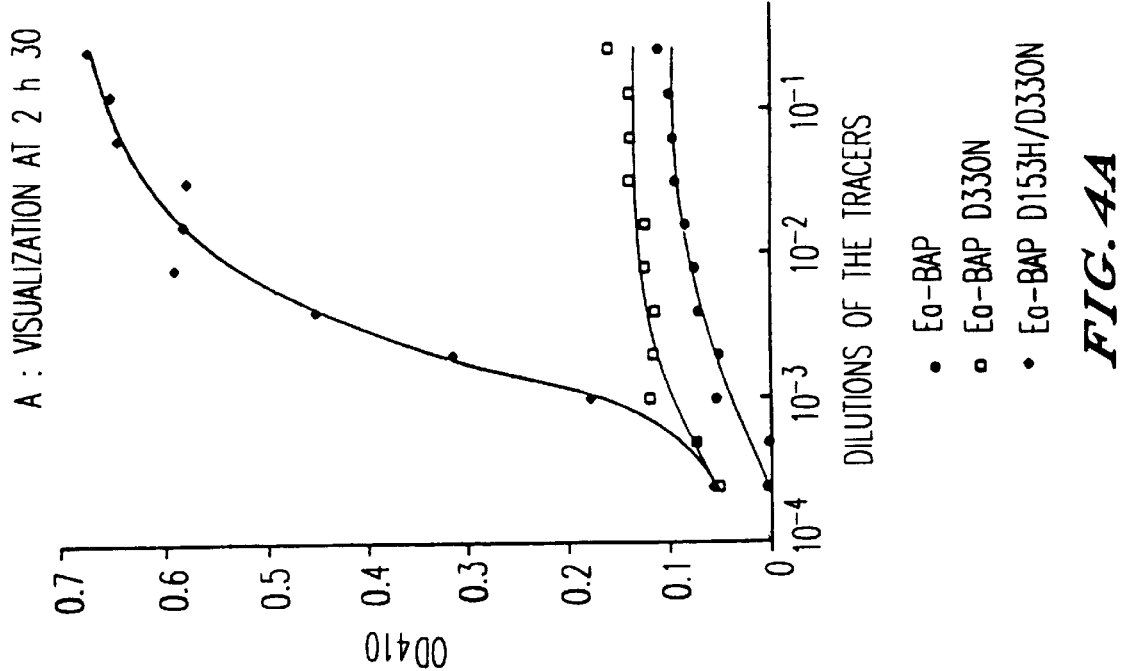

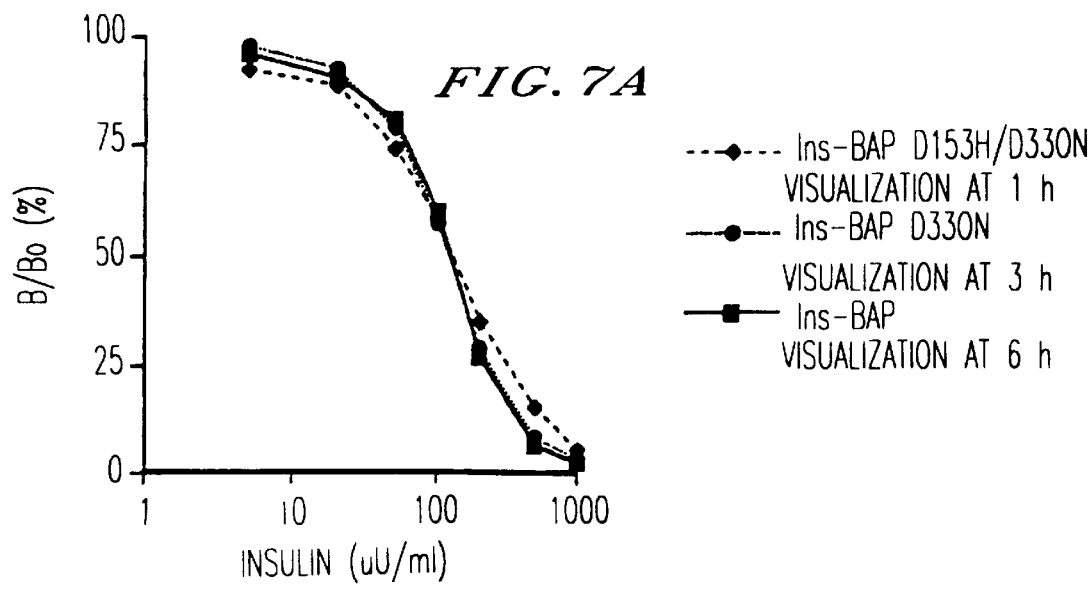
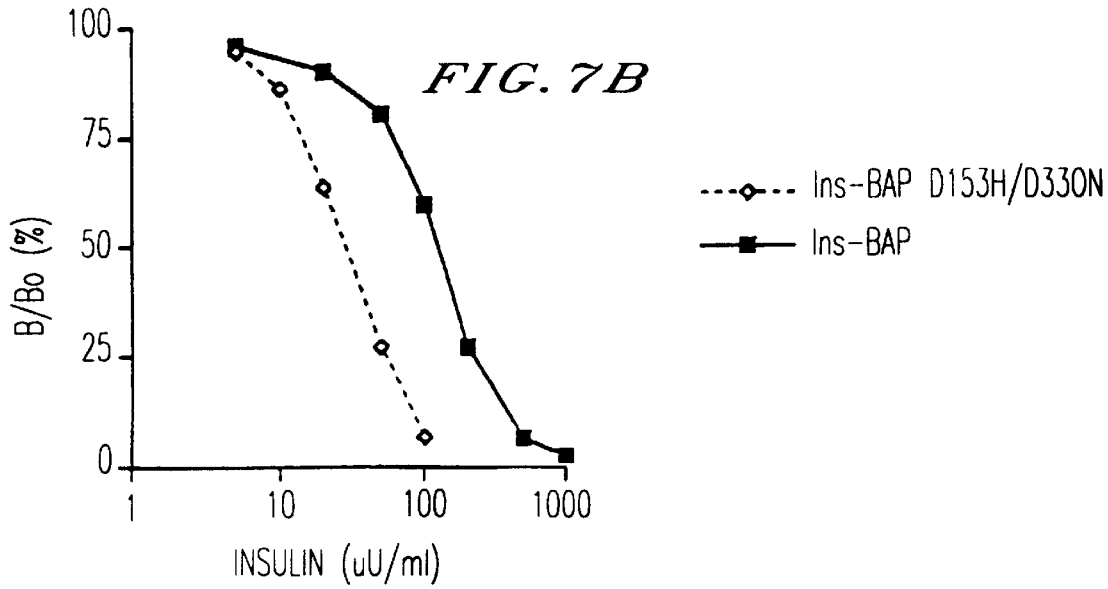

SEQUENCE LISTING ( 1 ) GENERAL INFORMATION:

( i i i ) NUMBER OF SEQUENCES: 10

( 2 ) INFORMATION FOR SEQ ID NO:1:

( i ) SEQUENCE CHARACTERISTICS:

( A ) LENGTH: 1443 base pairs

-continued (B) TYPE: nucleic acid
(C) STRANDEDNESS: single
(D) TOPOLOGY: linear (ii) MOLECULE TYPE: DNA (genomic)

(ix) FEATURE:
(A) NAME/KEY: CDS
(B) LOCATION: 64..1440

(xi) SEQUENCE DESCRIPTION: SEQ ID NO:1:

| GTGAAACAAA | GCACTATTGC | ACTGGCACTC | TTACCGTTAC | TGTTTACCCC | TGTGACAAAA | 60 |
|---|---|---|---|---|---|---|

| GCC | CGG | ACA | CCA | GAA | ATG | CCC | GTC | GAC | TTC | AGT | CGA | CGA | GCT | CCC | GGG | 108 |
|---|---|---|---|---|---|---|---|---|---|---|---|---|---|---|---|---|
| Arg | Thr | Pro | Glu | Met | Pro | Val | Asp | Phe | Ser | Arg | Arg | Ala | Pro | Gly | | |
| 1 | | | | 5 | | | | | 10 | | | | | 15 | | |

| GTT | CTG | GAA | AAC | CGG | GCT | GCT | CAG | GGC | GAT | ATT | ACT | GCA | CCC | GGC | GGT | 156 |
|---|---|---|---|---|---|---|---|---|---|---|---|---|---|---|---|---|
| Val | Leu | Glu | Asn | Arg | Ala | Ala | Gln | Gly | Asp | Ile | Thr | Ala | Pro | Gly | Gly | |
| | | | | 20 | | | | | 25 | | | | | 30 | | |

| GCT | CGC | CGT | TTA | ACG | GGT | GAT | CAG | ACT | GCC | GCT | CTG | CGT | GAT | TCT | CTT | 204 |
|---|---|---|---|---|---|---|---|---|---|---|---|---|---|---|---|---|
| Ala | Arg | Arg | Leu | Thr | Gly | Asp | Gln | Thr | Ala | Ala | Leu | Arg | Asp | Ser | Leu | |
| | | | | 35 | | | | | 40 | | | | | 45 | | |

| AGC | GAT | AAA | CCT | GCA | AAA | AAT | ATT | ATT | TTG | CTG | ATT | GGC | GAT | GGG | ATG | 252 |
|---|---|---|---|---|---|---|---|---|---|---|---|---|---|---|---|---|
| Ser | Asp | Lys | Pro | Ala | Lys | Asn | Ile | Ile | Leu | Leu | Ile | Gly | Asp | Gly | Met | |
| | | 50 | | | | | 55 | | | | | 60 | | | | |

| GGG | GAC | TCG | GAA | ATT | ACT | GCC | GCA | CGT | AAT | TAT | GCC | GAA | GGT | GCG | GGC | 300 |
|---|---|---|---|---|---|---|---|---|---|---|---|---|---|---|---|---|
| Gly | Asp | Ser | Glu | Ile | Thr | Ala | Ala | Arg | Asn | Tyr | Ala | Glu | Gly | Ala | Gly | |
| | 65 | | | | | 70 | | | | | 75 | | | | | |

| GGC | TTT | TTT | AAA | GGT | ATA | GAT | GCC | TTA | CCG | CTT | ACC | GGG | CAA | TAC | ACT | 348 |
|---|---|---|---|---|---|---|---|---|---|---|---|---|---|---|---|---|
| Gly | Phe | Phe | Lys | Gly | Ile | Asp | Ala | Leu | Pro | Leu | Thr | Gly | Gln | Tyr | Thr | |
| 80 | | | | | 85 | | | | | 90 | | | | | 95 | |

| CAC | TAT | GCG | CTG | AAT | AAA | AAA | ACC | GGC | AAA | CCG | GAC | TAC | GTC | ACC | GAC | 396 |
|---|---|---|---|---|---|---|---|---|---|---|---|---|---|---|---|---|
| His | Tyr | Ala | Leu | Asn | Lys | Lys | Thr | Gly | Lys | Pro | Asp | Tyr | Val | Thr | Asp | |
| | | | | 100 | | | | | 105 | | | | | 110 | | |

| TCG | GCT | GCA | TCA | GCA | ACC | GCC | TGG | TCA | ACC | GGT | GTC | AAA | ACC | TAT | AAC | 444 |
|---|---|---|---|---|---|---|---|---|---|---|---|---|---|---|---|---|
| Ser | Ala | Ala | Ser | Ala | Thr | Ala | Trp | Ser | Thr | Gly | Val | Lys | Thr | Tyr | Asn | |
| | | | 115 | | | | | 120 | | | | | 125 | | | |

| GGC | GCG | CTG | GGC | GTC | GAT | ATT | CAC | GAA | AAA | GAT | CAC | CCA | ACG | ATT | CTG | 492 |
|---|---|---|---|---|---|---|---|---|---|---|---|---|---|---|---|---|
| Gly | Ala | Leu | Gly | Val | Asp | Ile | His | Glu | Lys | Asp | His | Pro | Thr | Ile | Leu | |
| | | 130 | | | | | 135 | | | | | 140 | | | | |

| GAA | ATG | GCA | AAA | GCC | GCA | GGT | CTG | GCG | ACC | GGT | AAC | GTT | TCT | ACC | GCA | 540 |
|---|---|---|---|---|---|---|---|---|---|---|---|---|---|---|---|---|
| Glu | Met | Ala | Lys | Ala | Ala | Gly | Leu | Ala | Thr | Gly | Asn | Val | Ser | Thr | Ala | |
| 145 | | | | | 150 | | | | | 155 | | | | | | |

| GAG | TTG | CAG | CAC | GCC | ACG | CCC | GCT | GCG | CTG | GTG | GCA | CAT | GTG | ACC | TCG | 588 |
|---|---|---|---|---|---|---|---|---|---|---|---|---|---|---|---|---|
| Glu | Leu | Gln | His | Ala | Thr | Pro | Ala | Ala | Leu | Val | Ala | His | Val | Thr | Ser | |
| 160 | | | | | 165 | | | | | 170 | | | | | 175 | |

| CGC | AAA | TGC | TAC | GGT | CCG | AGC | GCG | ACC | AGT | GAA | AAA | TGT | CCG | GGT | AAC | 636 |
|---|---|---|---|---|---|---|---|---|---|---|---|---|---|---|---|---|
| Arg | Lys | Cys | Tyr | Gly | Pro | Ser | Ala | Thr | Ser | Glu | Lys | Cys | Pro | Gly | Asn | |
| | | | | 180 | | | | | 185 | | | | | 190 | | |

| GCT | CTG | GAA | AAA | GGC | GGA | AAA | GGA | TCG | ATT | ACC | GAA | CAG | CTG | CTT | AAC | 684 |
|---|---|---|---|---|---|---|---|---|---|---|---|---|---|---|---|---|
| Ala | Leu | Glu | Lys | Gly | Gly | Lys | Gly | Ser | Ile | Thr | Glu | Gln | Leu | Leu | Asn | |
| | | | 195 | | | | | 200 | | | | | 205 | | | |

| GCT | CGT | GCC | GAC | GTT | ACG | CTT | GGC | GGC | GGC | GCA | AAA | ACC | TTT | GCT | GAA | 732 |
|---|---|---|---|---|---|---|---|---|---|---|---|---|---|---|---|---|
| Ala | Arg | Ala | Asp | Val | Thr | Leu | Gly | Gly | Gly | Ala | Lys | Thr | Phe | Ala | Glu | |
| | | 210 | | | | | 215 | | | | | 220 | | | | |

| ACG | GCA | ACC | GCT | GGT | GAA | TGG | CAG | GGA | AAA | ACG | CTG | CGT | GAA | CAG | GCA | 780 |
|---|---|---|---|---|---|---|---|---|---|---|---|---|---|---|---|---|
| Thr | Ala | Thr | Ala | Gly | Glu | Trp | Gln | Gly | Lys | Thr | Leu | Arg | Glu | Gln | Ala | |
| | 225 | | | | | 230 | | | | | 235 | | | | | |

| CAG | GCG | CGT | GGT | TAT | CAG | TTG | GTG | AGC | GAT | GCT | GCC | TCA | CTG | AAT | TCG | 828 |
|---|---|---|---|---|---|---|---|---|---|---|---|---|---|---|---|---|
| Gln | Ala | Arg | Gly | Tyr | Gln | Leu | Val | Ser | Asp | Ala | Ala | Ser | Leu | Asn | Ser | |
| 240 | | | | | 245 | | | | | 250 | | | | | 255 | |

| GTG | ACG | GAA | GCG | AAT | CAG | CAA | AAA | CCC | CTG | CTT | GGC | CTG | TTT | GCT | GAC | 876 |
|---|---|---|---|---|---|---|---|---|---|---|---|---|---|---|---|---|
| Val | Thr | Glu | Ala | Asn | Gln | Gln | Lys | Pro | Leu | Leu | Gly | Leu | Phe | Ala | Asp | |

|     |     |     |     |     |     |     |     |     |     |     |     |     |     |     |     |      |
|-----|-----|-----|-----|-----|-----|-----|-----|-----|-----|-----|-----|-----|-----|-----|-----|------|
|     |     |     |     | 260 |     |     |     |     | 265 |     |     |     |     | 270 |     |      |
| GGC | AAT | ATG | CCA | GTG | CGC | TGG | CTA | GGA | CCG | AAA | GCA | ACG | TAC | CAT | GGC | 924  |
| Gly | Asn | Met | Pro | Val | Arg | Trp | Leu | Gly | Pro | Lys | Ala | Thr | Tyr | His | Gly |      |
|     |     |     | 275 |     |     |     | 280 |     |     |     |     | 285 |     |     |     |      |
| AAT | ATC | GAT | AAG | CCC | GCA | GTC | ACC | TGT | ACG | CCA | AAT | CCG | CAA | CGT | AAT | 972  |
| Asn | Ile | Asp | Lys | Pro | Ala | Val | Thr | Cys | Thr | Pro | Asn | Pro | Gln | Arg | Asn |      |
|     |     | 290 |     |     |     | 295 |     |     |     | 300 |     |     |     |     |     |      |
| GAC | AGT | GTA | CCA | ACC | CTG | GCG | CAG | ATG | ACC | GAC | AAA | GCC | ATT | GAA | TTG | 1020 |
| Asp | Ser | Val | Pro | Thr | Leu | Ala | Gln | Met | Thr | Asp | Lys | Ala | Ile | Glu | Leu |      |
|     | 305 |     |     |     | 310 |     |     |     |     | 315 |     |     |     |     |     |      |
| TTG | AGT | AAA | AAT | GAG | AAA | GGC | TTT | TTC | CTG | CAA | GTT | GAA | GGT | GCG | TCA | 1068 |
| Leu | Ser | Lys | Asn | Glu | Lys | Gly | Phe | Phe | Leu | Gln | Val | Glu | Gly | Ala | Ser |      |
| 320 |     |     |     | 325 |     |     |     |     | 330 |     |     |     |     | 335 |     |      |
| ATC | GAT | CAC | CAG | AAT | CAT | GCT | GCG | AAT | CCT | TGT | GGG | CAA | ATT | GGC | GAG | 1116 |
| Ile | Asp | His | Gln | Asn | His | Ala | Ala | Asn | Pro | Cys | Gly | Gln | Ile | Gly | Glu |      |
|     |     |     |     | 340 |     |     |     |     | 345 |     |     |     |     | 350 |     |      |
| ACG | GTC | GAT | CTC | GAT | GAA | GCC | GTA | CAA | CGG | GCG | CTG | GAA | TTC | GCT | AAA | 1164 |
| Thr | Val | Asp | Leu | Asp | Glu | Ala | Val | Gln | Arg | Ala | Leu | Glu | Phe | Ala | Lys |      |
|     |     |     | 355 |     |     |     |     | 360 |     |     |     |     | 365 |     |     |      |
| AAG | GAG | GGT | AAC | ACG | CTG | GTC | ATA | GTC | ACC | GCT | GAT | CAC | GCC | CAC | GCC | 1212 |
| Lys | Glu | Gly | Asn | Thr | Leu | Val | Ile | Val | Thr | Ala | Asp | His | Ala | His | Ala |      |
|     |     | 370 |     |     |     |     | 375 |     |     |     |     | 380 |     |     |     |      |
| AGC | CAG | ATT | GTT | GCG | CCG | GAT | ACC | AAA | GCT | CCG | GGC | CTC | ACC | CAG | GCG | 1260 |
| Ser | Gln | Ile | Val | Ala | Pro | Asp | Thr | Lys | Ala | Pro | Gly | Leu | Thr | Gln | Ala |      |
|     | 385 |     |     |     |     | 390 |     |     |     |     | 395 |     |     |     |     |      |
| CTA | AAT | ACC | AAA | GAT | GGC | GCA | GTG | ATG | GTG | ATG | AGT | TAC | GGG | AAC | TCC | 1308 |
| Leu | Asn | Thr | Lys | Asp | Gly | Ala | Val | Met | Val | Met | Ser | Tyr | Gly | Asn | Ser |      |
| 400 |     |     |     |     | 405 |     |     |     |     | 410 |     |     |     |     | 415 |      |
| GAA | GAG | GAT | TCA | CAA | GAA | CAT | ACC | GGC | AGT | CAG | TTG | CGT | ATT | GCG | GCG | 1356 |
| Glu | Glu | Asp | Ser | Gln | Glu | His | Thr | Gly | Ser | Gln | Leu | Arg | Ile | Ala | Ala |      |
|     |     |     |     | 420 |     |     |     |     | 425 |     |     |     |     | 430 |     |      |
| TAT | GGC | CCG | CAT | GCC | GCC | AAT | GTT | GTT | GGA | CTG | ACC | GAC | CAG | ACC | GAT | 1404 |
| Tyr | Gly | Pro | His | Ala | Ala | Asn | Val | Val | Gly | Leu | Thr | Asp | Gln | Thr | Asp |      |
|     |     |     | 435 |     |     |     |     | 440 |     |     |     |     | 445 |     |     |      |
| CTC | TTC | TAC | ACC | ATG | AAA | GCC | GCT | CTG | GGG | CTG | AAA | TAA |     |     |     | 1443 |
| Leu | Phe | Tyr | Thr | Met | Lys | Ala | Ala | Leu | Gly | Leu | Lys |     |     |     |     |      |
|     |     | 450 |     |     |     |     | 455 |     |     |     |     |     |     |     |     |      |

( 2 ) INFORMATION FOR SEQ ID NO:2:

( i ) SEQUENCE CHARACTERISTICS:
  ( A ) LENGTH: 459 amino acids
  ( B ) TYPE: amino acid
  ( D ) TOPOLOGY: linear ( i i ) MOLECULE TYPE: protein ( x i ) SEQUENCE DESCRIPTION: SEQ ID NO:2:

| Arg | Thr | Pro | Glu | Met | Pro | Val | Asp | Phe | Ser | Arg | Arg | Ala | Pro | Gly | Val |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |
| Leu | Glu | Asn | Arg | Ala | Ala | Gln | Gly | Asp | Ile | Thr | Ala | Pro | Gly | Gly | Ala |
|     |     |     | 20  |     |     |     |     | 25  |     |     |     |     | 30  |     |     |
| Arg | Arg | Leu | Thr | Gly | Asp | Gln | Thr | Ala | Ala | Leu | Arg | Asp | Ser | Leu | Ser |
|     |     | 35  |     |     |     |     | 40  |     |     |     |     | 45  |     |     |     |
| Asp | Lys | Pro | Ala | Lys | Asn | Ile | Ile | Leu | Leu | Ile | Gly | Asp | Gly | Met | Gly |
|     | 50  |     |     |     |     | 55  |     |     |     |     | 60  |     |     |     |     |
| Asp | Ser | Glu | Ile | Thr | Ala | Ala | Arg | Asn | Tyr | Ala | Glu | Gly | Ala | Gly | Gly |
| 65  |     |     |     |     | 70  |     |     |     |     | 75  |     |     |     |     | 80  |
| Phe | Phe | Lys | Gly | Ile | Asp | Ala | Leu | Pro | Leu | Thr | Gly | Gln | Tyr | Thr | His |
|     |     |     |     | 85  |     |     |     |     | 90  |     |     |     |     | 95  |     |

```
Tyr Ala Leu Asn Lys Lys Thr Gly Lys Pro Asp Tyr Val Thr Asp Ser
            100                 105                 110

Ala Ala Ser Ala Thr Ala Trp Ser Thr Gly Val Lys Thr Tyr Asn Gly
            115                 120                 125

Ala Leu Gly Val Asp Ile His Glu Lys Asp His Pro Thr Ile Leu Glu
        130                 135                 140

Met Ala Lys Ala Ala Gly Leu Ala Thr Gly Asn Val Ser Thr Ala Glu
145                 150                 155                 160

Leu Gln His Ala Thr Pro Ala Ala Leu Val Ala His Val Thr Ser Arg
                165                 170                 175

Lys Cys Tyr Gly Pro Ser Ala Thr Ser Glu Lys Cys Pro Gly Asn Ala
            180                 185                 190

Leu Glu Lys Gly Gly Lys Gly Ser Ile Thr Glu Gln Leu Leu Asn Ala
            195                 200                 205

Arg Ala Asp Val Thr Leu Gly Gly Ala Lys Thr Phe Ala Glu Thr
    210                 215                 220

Ala Thr Ala Gly Glu Trp Gln Gly Lys Thr Leu Arg Glu Gln Ala Gln
225                 230                 235                 240

Ala Arg Gly Tyr Gln Leu Val Ser Asp Ala Ser Leu Asn Ser Val
            245                 250                 255

Thr Glu Ala Asn Gln Gln Lys Pro Leu Leu Gly Leu Phe Ala Asp Gly
            260                 265                 270

Asn Met Pro Val Arg Trp Leu Gly Pro Lys Ala Thr Tyr His Gly Asn
            275                 280                 285

Ile Asp Lys Pro Ala Val Thr Cys Thr Pro Asn Pro Gln Arg Asn Asp
            290                 295                 300

Ser Val Pro Thr Leu Ala Gln Met Thr Asp Lys Ala Ile Glu Leu Leu
305                 310                 315                 320

Ser Lys Asn Glu Lys Gly Phe Phe Leu Gln Val Glu Gly Ala Ser Ile
            325                 330                 335

Asp His Gln Asn His Ala Ala Asn Pro Cys Gly Gln Ile Gly Glu Thr
            340                 345                 350

Val Asp Leu Asp Glu Ala Val Gln Arg Ala Leu Glu Phe Ala Lys Lys
            355                 360                 365

Glu Gly Asn Thr Leu Val Ile Val Thr Ala Asp His Ala His Ala Ser
            370                 375                 380

Gln Ile Val Ala Pro Asp Thr Lys Ala Pro Gly Leu Thr Gln Ala Leu
385                 390                 395                 400

Asn Thr Lys Asp Gly Ala Val Met Val Met Ser Tyr Gly Asn Ser Glu
            405                 410                 415

Glu Asp Ser Gln Glu His Thr Gly Ser Gln Leu Arg Ile Ala Ala Tyr
            420                 425                 430

Gly Pro His Ala Ala Asn Val Val Gly Leu Thr Asp Gln Thr Asp Leu
            435                 440                 445

Phe Tyr Thr Met Lys Ala Ala Leu Gly Leu Lys
450                 455
```

( 2 ) INFORMATION FOR SEQ ID NO:3:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( i i ) MOLECULE TYPE: other nucleic acid -continued ( x i ) SEQUENCE DESCRIPTION: SEQ ID NO:3:

TGTACAAATA CATTAAAGGA TCCAAACAAA GCGACTAT    38

( 2 ) INFORMATION FOR SEQ ID NO:4:

( i ) SEQUENCE CHARACTERISTICS:
        ( A ) LENGTH: 34 base pairs
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:4:

GATTCGCAGC ATGATGACCG TGATCGATTG ACGC    34

( 2 ) INFORMATION FOR SEQ ID NO:5:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:5:

AACAACATTG GCGGCATGCG GGCC    24

( 2 ) INFORMATION FOR SEQ ID NO:6:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:6:

GACTTCAGTC GACGAGCTCC CGGG    24

( 2 ) INFORMATION FOR SEQ ID NO:7:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:7:

GAAATGCCCG TCGACAGGAT ATGTTTTAAC    30

( 2 ) INFORMATION FOR SEQ ID NO:8:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: other nucleic acid ( x i ) SEQUENCE DESCRIPTION: SEQ ID NO:8:

GAACCCCGGG AGCTCCATTG TTGCAGACCT    30

( 2 ) INFORMATION FOR SEQ ID NO:9:

( i ) SEQUENCE CHARACTERISTICS:
        ( A ) LENGTH: 6162 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:9:

```
AAGCTTTGGA  GATTATCGTC  ACTGCAATGC  TTCGCAATAT  GGCGCAAAAT  GACCAACAGC     60
GGTTGATTGA  TCAGGTAGAG  GGGGCGCTGT  ACGAGGTAAA  GCCCGATGCC  AGCATTCCTG    120
ACGACGATAC  GGAGCTGCTG  CGCGATTACG  TAAAGAAGTT  ATTGAAGCAT  CCTCGTCAGT    180
AAAAGTTAA   TCTTTTCAAC  AGCTGTCATA  AAGTTGTCAC  GGCCGAGACT  TATAGTCGCT    240
TTGTTTGGAT  CCTTTAATGT  ATTTGTACAT  GGAGAAAATA  AAGTGAAACA  AAGCACTATT    300
GCACTGGCAC  TCTTACCGTT  ACTGTTTACC  CCTGTGACAA  AAGCCCGGAC  ACCAGAAATG    360
CCCGTCGACT  TCAGTCGACG  AGCTCCCGGG  GTTCTGGAAA  ACCGGGCTGC  TCAGGGCGAT    420
ATTACTGCAC  CCGGCGGTGC  TCGCCGTTTA  ACGGGTGATC  AGACTGCCGC  TCTGCGTGAT    480
TCTCTTAGCG  ATAAACCTGC  AAAAAATATT  ATTTTGCTGA  TTGGCGATGG  GATGGGGGAC    540
TCGGAAATTA  CTGCCGCACG  TAATTATGCC  GAAGGTGCGG  GCGGCTTTTT  TAAAGGTATA    600
GATGCCTTAC  CGCTTACCGG  GCAATACACT  CACTATGCGC  TGAATAAAAA  AACCGGCAAA    660
CCGGACTACG  TCACCGACTC  GGCTGCATCA  GCAACCGCCT  GGTCAACCGG  TGTCAAAACC    720
TATAACGGCG  CGCTGGGCGT  CGATATTCAC  GAAAAGATC   ACCCAACGAT  TCTGGAAATG    780
GCAAAAGCCG  CAGGTCTGGC  GACCGGTAAC  GTTTCTACCG  CAGAGTTGCA  GGATGCCACG    840
CCCGCTGCGC  TGGTGGCACA  TGTGACCTCG  CGCAAATGCT  ACGGTCCGAG  CGCGACCAGT    900
GAAAATGTC   CGGGTAACGC  TCTGGAAAAA  GGCGGAAAAG  GATCGATTAC  CGAACAGCTG    960
CTTAACGCTC  GTGCCGACGT  TACGCTTGGC  GGCGGCGCAA  AAACCTTTGC  TGAAACGGCA   1020
ACCGCTGGTG  AATGGCAGGG  AAAAACGCTG  CGTGAACAGG  CACAGGCGCG  TGGTTATCAG   1080
TTGGTGAGCG  ATGCTGCCTC  ACTGAATTCG  GTGACGGAAG  CGAATCAGCA  AAAACCCCTG   1140
CTTGGCCTGT  TTGCTGACGG  CAATATGCCA  GTGCGCTGGC  TAGGACCGAA  AGCAACGTAC   1200
CATGGCAATA  TCGATAAGCC  CGCAGTCACC  TGTACGCCAA  ATCCGCAACG  TAATGACAGT   1260
GTACCAACCC  TGGCGCAGAT  GACCGACAAA  GCCATTGAAT  TGTTGAGTAA  AAATGAGAAA   1320
GGCTTTTTCC  TGCAAGTTGA  AGGTGCGTCA  ATCGATAAAC  AGGATCATGC  TGCGAATCCT   1380
TGTGGGCAAA  TTGGCGAGAC  GGTCGATCTC  GATGAAGCCG  TACAACGGGC  GCTGGAATTC   1440
GCTAAAAAGG  AGGGTAACAC  GCTGGTCATA  GTCACCGCTG  ATCACGCCCA  CGCCAGCCAG   1500
ATTGTTGCGC  CGGATACCAA  AGCTCCGGGC  CTCACCCAGG  CGCTAAATAC  CAAAGATGGC   1560
GCAGTGATGG  TGATGAGTTA  CGGGAACTCC  GAAGAGGATT  CACAAGAACA  TACCGGCAGT   1620
CAGTTGCGTA  TTGCGGCGTA  TGGCCCGCAT  GCCGCCAATG  TTGTTGGACT  GACCGACCAG   1680
ACCGATCTCT  TCTACACCAT  GAAAGCCGCT  CTGGGGCTGA  AATAAACCG   CGCCGGCAG    1740
TGAATTTTCG  CTGCCGGGTG  GTTTTTTTGC  TGTTAGCAAC  CAGACTTAAT  GGCAGATCAC   1800
GGGCGCATAC  GCTCATGGTT  AAAACATGAA  GAGGGATGGT  GCTATGAAAA  TAACATTACT   1860
GGTTACCTTG  CTTTTCGGTC  TGGTTTTTTT  AACCACCGTC  GGCGCTGCCG  AGAGAACTTT   1920
AACCCCACAA  CAACAGCGTA  TGACCTCCTG  TAATCAGCAG  GCGACGGCGC  AGGCGTTGAA   1980
AGGGGATGCT  CGTAAGACCT  ACATGAGTGA  TTGCCTGAAG  AACAGCAAGT  CTGCGCCTGG   2040
```

| | | | | | |
|---|---|---|---|---|---|
| CGAAAAAAGT | TTGACGCCAC | AGCAGCAAAA | GATGCGCGAA | TGCAATAATC | AAGCAACACA | 2100
| ACAATCTCTG | AAAGGTGATG | ATCGTAATAA | GTTTATGAGT | GCCTGCCTCA | AGAAAGCCGC | 2160
| CTGATACCTG | ATAGTGCTAA | CGGGTGAGCT | ACGAAAATGG | CTCACCCGAA | ATATCATACT | 2220
| TCTGCCTTTA | GCTCCGTCTC | TATAATTTGG | GAAAATTGTT | TCTGAATGTT | CCCAAAAATA | 2280
| ATGAATGATG | AAAACTTTTT | CAAAAAGCG | GCGGCGCACG | GGGAGGAACC | TCCTTTAACT | 2340
| CCTCAAAACG | AACATCAGCG | GTCCGGGCTG | CGCTTCGCCC | GTCGCGTCAG | ACTACCCCGT | 2400
| GCGGTTGGCC | TGGCTGGCAT | GTTCTTACCG | ATTGCTTCAA | CGCTGGTTTC | ACACCCGCCG | 2460
| CCGGGCTGGT | GGTGGCTGGT | GTTGGTCGGC | TGGGCGTTCG | TCTGGCCGCA | TTTAGCCTGG | 2520
| CAGATAGCGA | GCAGGGCCGT | CGATCCGCTT | AGCCGGGAAA | TTTACAACTT | AAAAACCGAT | 2580
| GCAGTATTAG | CGGGAATGTG | GGTAGGCGTA | ATGGGCGTAA | ACGTGCTGCC | TTCCACCGCG | 2640
| ATGTTGATGA | TTATGTGTCT | GAATTTGATG | GGGCAGGCG | GCCCCGTCT | GTTTGTCGCG | 2700
| GGTCTGGTGT | TGATGGTGGT | TTCCTGCCTT | GTCACCCTCG | AGCAAGACGT | TTCCCGTTGA | 2760
| ATATGGCTCA | TAACACCCCT | TGTATTACTG | TTTATGTAAG | CAGACAGTTT | TATTGTTCAT | 2820
| GATGATATAT | TTTTATCTTG | TGCAATGTAA | CATCAGAGAT | TTTGAGACAC | AACGTGGCTT | 2880
| TGTTGAATAA | ATCGAACTTT | TGCTGAGTTG | AAGGATCAGA | TCACGCATCT | TCCCGACAAC | 2940
| GCAGACCGTT | CCGTGGCAAA | GCAAAGTTC | AAAATCACCA | ACTGGTCCAC | CTACAACAAA | 3000
| GCTCTCATCA | ACCGTGGCTC | CCTCACTTTC | TGGCTGGATG | ATGGGGCGAT | TCAGGCCTGG | 3060
| TATGAGTCAG | CAACACCTTC | TTCACGAGGC | AGACCTCAGC | GCTAGCGGAC | TGTATACTGG | 3120
| CTTACTATGT | TGGCACTGAT | GAGGGTGTCA | GTGAAGTGCT | TCATGTGGCA | GGAGAAAAA | 3180
| GGCTGCACCG | GTGCGTCAGC | AGAATATGTG | ATACAGGATA | TATTCCGCTT | CCTCGCTCAC | 3240
| TGACTCGCTA | CGCTCGGTCG | TTCGACTGCG | GCGAGCGGAA | ATGGCTTACG | AACGGGGCGG | 3300
| AGATTTCCTG | GAAGATGCCA | GGAAGATACT | TAACAGGGAA | GTGAGAGGGC | CGCGGCAAAG | 3360
| CCGTTTTTCC | ATAGGCTCCG | CCCCCCTGAC | AAGCATCACG | AAATCTGACG | CTCAAATCAG | 3420
| TGGTGGCGAA | ACCCGACAGG | ACTATAAAGA | TACCAGGCGT | TTCCCCCTGG | CGGCTCCCTC | 3480
| GTGCGCTCTC | CTGTTCCTGC | CTTTCGGTTT | ACCGGTGTCA | TTCCGCTGTT | ATGGCCGCGT | 3540
| TTGTCTCATT | CCACGCCTGA | CACTCAGTTC | CGGGTAGGCA | GTTCGCTCCA | AGCTGGACTG | 3600
| TATGCACGAA | CCCCCCGTTC | AGTCCGACCG | CTGCGCCTTA | TCCGGTAACT | ATCGTCTTGA | 3660
| GTCCAACCCG | GAAAGACATG | CAAAAGCACC | ACTGGCAGCA | GCCACTGGTA | ATTGATTTAG | 3720
| AGGAGTTAGT | CTTGAAGTCA | TGCGCCGGTT | AAGGCTAAAC | TGAAAGGACA | AGTTTTGGTG | 3780
| ACTGCGCTCC | TCCAAGCCAG | TTACCTCGGT | TCAAAGAGTT | GGTAGCTCAG | AGAACCTTCG | 3840
| AAAAACCGCC | CTGCAAGGCG | GTTTTTTCGT | TTTCAGAGCA | AGAGATTACG | CGCAGACCAA | 3900
| AACGATCTCA | AGAAGATCAT | CTTATTAAGG | GGTCTGACGC | TCAGTGGAAC | GAAAACTCAC | 3960
| GTTAAGGGAT | TTTGGTCATG | AGATTATCAA | AAAGGATCTT | CACCTAGATC | CTTTTAAATT | 4020
| AAAAATGAAG | TTTTAAATCA | ATCTAAAGTA | TATATGAGTA | AACTTGGTCT | GACAGTTACC | 4080
| AATGCTTAAT | CAGTGAGGCA | CCTATCTCAG | CGATCTGTCT | ATTTCGTTCA | TCCATAGTTG | 4140
| CCTGACTCCC | CGTCGTGTAG | ATAACTACGA | TACGGGAGGG | CTTACCATCT | GGCCCCAGTG | 4200
| CTGCAATGAT | ACCGCGAGAC | CCACGCTCAC | CGGCTCCAGA | TTTATCAGCA | ATAAACCAGC | 4260
| CAGCCGGAAG | GGCCGAGCGC | AGAAGTGGTC | CTGCAACTTT | ATCCGCCTCC | ATCCAGTCTA | 4320
| TTAATTGTTG | CCGGGAAGCT | AGAGTAAGTA | GTTCGCCAGT | TAATAGTTTG | CGCAACGTTG | 4380
| TTGCCATTGC | TGCAGGCATC | GTGGTGTCAC | GCTCGTCGTT | TGGTATGGCT | TCATTCAGCT | 4440

-continued

| | | | | | |
|---|---|---|---|---|---|
| CCGGTTCCCA | ACGATCAAGG | CGAGTTACAT | GATCCCCCAT | GTTGTGCAAA | AAAGCGGTTA | 4500
| GCTCCTTCGG | TCCTCCGATC | GTTGTCAGAA | GTAAGTTGGC | CGCAGTGTTA | TCACTCATGG | 4560
| TTATGGCAGC | ACTGCATAAT | TCTCTTACTG | TCATGCCATC | CGTAAGATGC | TTTTCTGTGA | 4620
| CTGGTGAGTA | CTCAACCAAG | TCATTCTGAG | AATAGTGTAT | GCGGCGACCG | AGTTGCTCTT | 4680
| GCCCGGCGTC | AACACGGGAT | AATACCGCGC | CACATAGCAG | AACTTTAAAA | GTGCTCATCA | 4740
| TTGGAAAACG | TTCTTCGGGG | CGAAAACTCT | CAAGGATCTT | ACCGCTGTTG | AGATCCAGTT | 4800
| CGATGTAACC | CACTCGTGCA | CCCAACTGAT | CTTCAGCATC | TTTTACTTTC | ACCAGCGTTT | 4860
| CTGGGTGAGC | AAAAACAGGA | AGGCAAAATG | CCGCAAAAAA | GGGAATAAGG | GCGACACGGA | 4920
| AATGTTGAAT | ACTCATACTC | TTCCTTTTTC | AATATTATTG | AAGCATTTAT | CAGGGTTATT | 4980
| GTCTCATGAG | CGGATACATA | TTTGAATGTA | TTTAGAAAAA | TAAACAAATA | GGGGTTCCGC | 5040
| GCACATTTCC | CCGAAAAGTG | CCACCTGACG | TCTAAGAAAC | CATTATTATC | ATGACATTAA | 5100
| CCTATAAAAA | TAGGCGTATG | CACGAGGCCC | TTTCGTCTTC | AAGAATTTTA | TAAACCGTGG | 5160
| AGCGGGCAAT | ACTGAGCTGA | TGAGCAATTT | CCGTTGCACC | AGTGCCCTTC | TGATGAAGCG | 5220
| TCAGCACGAC | GTTCCTGTCC | ACGGTACGCC | TGCGGCCAAA | TTTGATTCCT | TTCAGCTTTG | 5280
| CTTCCTGTCG | GCCCTCATTC | GTGCGCTCTA | GGATCCTCCG | GCGTTCAGCC | TGTGCCACAG | 5340
| CCGACAGGAT | GGTGACCACC | ATTTGCCCCA | TATCACCGTC | GGTACTGATC | CCGTCGTCAA | 5400
| TAAACCGAAC | CGCTACACCC | TGAGCATCAA | ACTCTTTTAT | CAGTTGGATC | ATGTCGGCGT | 5460
| GTCGCGGCCA | AGACGGTCGA | GCTTCTTCAC | CAGAATGACA | TCACCTTCCT | CCACCTTCAT | 5520
| CCTCAGCAAA | TCCAGCCCTT | CCCGATCTGT | TGAACTGCCG | GATGCCTTGT | CGGTAAAGAT | 5580
| GCGGTTAGCT | TTTACCCCTG | CATCTTTGAG | CGCTGAGGTC | TGCCTCGTGA | AGAAGGTGTT | 5640
| GCTGACTCAT | ACCAGGCCTG | AATCGCCCCA | TCATCCAGCC | AGAAAGTGAG | GGAGCCACGG | 5700
| TTGATGAGAG | CTTTGTTGTA | GGTGGACCAG | TTGGTGATTT | TGAACTTTTG | CTTTGCCACG | 5760
| GAACGGTCTG | CGTTGTCGGG | AAGATGCGTG | ATCTGATCCT | TCAACTCAGC | AAAAGTTCGA | 5820
| TTTATTCAAC | AAAGCCGCCG | TCCCGTCAAG | TCAGCGTAAT | GCTCTGCCAG | TGTTACAACC | 5880
| AATTAACCAA | TTCTGATTAG | AAAAACTCAT | CGAGCATCAA | ATGAAACTGC | AATTTATTCA | 5940
| TATCAGGATT | ATCAATACCA | TATTTTTGAA | AAAGCCGTTT | CTGTAATGAA | GGAGAAAACT | 6000
| CACCGAGGCA | GTTCCATAGG | ATGGCAAGAT | CCTGGTATCG | GTCTGCGATT | CCGACTCGTC | 6060
| CAACATCAAT | ACAACCTATT | AATTTCCCCC | TCGTCAAAAA | TAAGGTTATC | AAGTGAGAAA | 6120
| TCACCATGAG | TGACGACTGA | ATCCGGTGAG | AATGGCAATT | CG | | 6162

( 2 ) INFORMATION FOR SEQ ID NO:10:

( i ) SEQUENCE CHARACTERISTICS:
        ( A ) LENGTH: 269 base pairs
        ( B ) TYPE: nucleic acid
        ( C ) STRANDEDNESS: double
        ( D ) TOPOLOGY: linear ( i i ) MOLECULE TYPE: other nucleic acid ( x i ) SEQUENCE DESCRIPTION: SEQ ID NO:10:

| | | | | | |
|---|---|---|---|---|---|
| TCGACTTCGT | TAACCAGCAC | CTGTGCGGGT | CCCACCTGGT | GGAAGCTTTG | TATCTGGTGT | 60
| GCGGCGAGCG | TGGCTTCTTC | TACACCCCGA | AGACGCGTCG | TGAAGCGGAA | GATCTGCAAG | 120

-continued

```
TGGGCCAGGT  GGAACTGGGC  GGGGGCCCGG  GCGCCGGCAG  CCTGCAACCG  CTGGCGCTGG      180

AGGGCAGCCT  CCAGAAGCGT  GGCATTGTGG  AGCAGTGTTG  TACTAGTATC  TGCAGCCTGT      240

ACCAGCTGGA  GAATTACTGC  AACGGAGCT                                           269
```

MODIFIED BACTERIAL ALKALINE PHOSPHATASES AND THEIR APPLICATIONS

The present invention relates to modified bacterial alkaline phosphatases (BAP or bacterial alkaline phosphatase) exhibiting, at one and the same time, significantly improved enzymic properties and increased thermal stability, and to their applications, in particular in immunoenzymic assays (reagents and diagnostic kits.

The present invention also relates to a method for obtaining mutants which possess significantly improved enzymic properties.

Alkaline phosphatase is a non-specific phosphomonoesterase. This dimeric metalloenzyme consists of two identical polypeptide chains, each of which contains two zinc atoms and one magnesium atom, which atoms are located at the heart of the catalytic site.

The catalytic mechanism comprises several steps, including the formation of a covalent phosphoryl-enzyme (E-$P_i$) intermediate complex with serine 102 of the protein, in accordance with the following reaction:

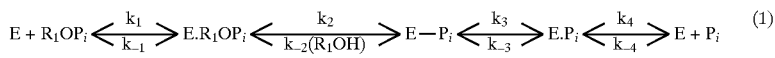

The catalytic constant of the reaction ($k_{cat}$) depends on the limiting step of the process. At acid pH, the limiting factor is the rupture of the covalent E-$P_i$ bond; at alkaline pH, it is the dissociation of the non-covalent E.$P_i$ complex which is the limiting step (BUTLER-RANSOHOFF et al., J. Org. Chem. 1992, 57, 142–145).

In the presence of a phosphate acceptor ($R_2OH$), such as ethanolamine or Tris, the enzyme catalyses a transphosphorylation reaction with the transfer of the phosphoryl group to the alcohol, in accordance with formula (2) below:

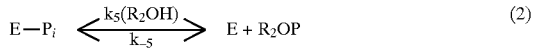

The catalytic efficiency is measured by the $k_{cat}/K_m$ ratio, which takes into account both the hydrolytic activity and the substrate affinity of the enzyme.

Alkaline phosphatase is found in all organisms, from bacteria to mammals.

The enzymes present in mammals possess the highest specific activities; it is for this reason that calf intestinal alkaline phosphatase (CIP=calf intestinal phosphatase) is normally selected for constructing immunoenzymic reagents which are used in in-vitro diagnostic tests. However, CIP is difficult to purify in a reproducible manner and has poor thermal stability.

Bacterial alkaline phosphatase (BAP), which exhibits an enzyme activity which is significantly lower than that of the CIP, is produced in large quantities by E. coli; it can easily be purified and possesses exceptional thermal stability. Furthermore, it can be used for constructing immunoenzymic reagents using gene fusion techniques.

As a consequence, various groups have attempted to improve the catalytic properties of the bacterial enzyme with the aim of substituting it for CIP in the preparation of assay reagents.

The introduction of point mutations into the active site of BAP has made it possible to obtain molecules which possess an enzyme activity which is increased as compared with the wild-type enzyme:

CHAIDAROGLOU and KANTROWITZ (*Protein Engineering*, 1989, 3, 2, 127–132) have described a mutant of E. coli BAP in which the aspartic acid at position 101 is replaced by alanine (mutant designated D101A). While, at pH 9.4 and in the presence of a phosphate acceptor, such a mutant exhibits a catalytic activity which is three-fold greater than that of the wild-type enzyme, it also exhibits a clear decrease in the stability towards heat.

The thermal stability studies were carried out under different conditions from those which are normally allowed; nevertheless, they clearly demonstrate that the mutant has a thermal stability which is inferior to that of the wild-type enzyme.

European patent application 0 441 252, in the name of Abbott Laboratories, describes, with a view to using them as reagents, alkaline phosphatases which have an improved specific activity (catalytic activity thirty-six-fold greater than that of the wild-type enzyme), at pH 10 and in the presence of low concentrations of either Tris, 0.05M, or diethanolamine, 0.05M, but which exhibit decreased thermal stability. The mutations which are described in this application are located either at a distance of approximately 20 Å from the active site of the enzyme, or at a distance of approximately 10 Å from the active site of the enzyme, or in the active site, and include:

(i) mutations which only involve one single amino acid, such as:
replacement of Thr[100] by Val or Ile (mutants T100V or T100I)
replacement of Lys[328] by Arg (mutant L328R)
replacement of Val[99] by Ala (mutant V99A)
replacement of Ala[103] by Asp or Cys (mutants A103D or A103C)
replacement of Thr[107] by Val (mutant T107V)
replacement of Asp[101] by Ser (mutant D101S)

(ii) mutations affecting two amino acids, such as:
replacement of Val[99] by Ala and of Lys[328] by Arg (mutant V99A and K328R)
replacement of Val[377] by Ala and of Ser[415] by Gly (mutant V377A and S415G).

International application PCT WO 94/01531, which is also in the name of Abbott Laboratories and which essentially incorporates the content of the abovementioned European application additionally describes the replacement of Asp[153] by Gly (mutant D153G).

As a general rule, in order to measure a catalytic activity, it is necessary to place a given enzyme under conditions which are optimal for its activity; however, in these Abbott applications, the activities of the wild-type enzyme and of the mutants are compared under the same conditions, in the event under conditions which are optimal for the mutants.

As a consequence, in the case of the Abbott applications, the increase in the catalytic activity by a factor of 36 results from comparing the catalytic activity of the mutant, which has been placed under functionally optimal conditions, with the catalytic activity of the wild-type enzyme under the same conditions. If these activities are compared under conditions which are functionally optimal for each of the enzymes, the factor by which the catalytic properties increase is limited to 18.

Furthermore, none of these mutants (which only differ from the wild-type BAP by one or two residues at most) succeeds in procuring for the modified alkaline phosphatase both an enzyme activity which is equivalent to that of the corresponding mammalian enzyme and a thermal stability which is significantly superior to that of the mammalian enzyme and, in particular, the thermal stability of the initial bacterial enzyme.

Other studies have been carried out, the objective of which was to achieve a better understanding of the catalytic mechanism of the enzyme. More precisely, the authors of these various articles have attempted to determine the molecular reasons behind the differences which have been observed between BAP and the mammalian enzymes: the 20 to 30-fold higher enzyme activity of the mammalian enzymes, displacement of the optimum activity towards high pH values, and the necessity of adding magnesium in order to obtain maximum activity. Within the region of the active site, there are two notable differences between the bacterial enzymes and the mammalian enzymes. In the bacterial enzymes, positions 153 and 328 are occupied by Asp and Lys residues, respectively, whereas a His residue is present at these two positions in the mammalian enzymes. In order to assess the importance of these differences for the enzyme activity, His residues were introduced into these two positions in the bacterial enzyme (XU and KANTROWITZ, Biochemistry, 1991, 30, 7789–7796; JANEWAY et al., Biochemistry, 1993, 32, 1601–1609).

XU and KANTROWITZ describe, in particular, the replacement of the lysine in position 328 by a histidine and the properties of the mutant which was obtained (K328H). In the presence of a phosphate acceptor, mutant K328H has an activity which is comparable to that of the wild-type enzyme; by contrast, at pH 8 and in the absence of a phosphate acceptor, this mutant exhibits a significant decrease in catalytic activity, as compared with that of the wild-type enzyme. These results suggest that these mutations lead to an inhibition of hydrolytic activity which is accompanied by an increase in transphosphorylation activity. Furthermore, this mutant has a decreased affinity for phosphate. In summary, such a mutation brings about:—a displacement of the optimum enzyme activity towards pH 10,—an increase in the specific activity (especially transferase activity) and—a fall in affinity for the substrate and for inorganic phosphate $P_i$, at pH 10.

Without doubt, this fall in affinity for $P_i$ is linked to the elimination of the bond to $P_i$, by the mediation of a molecule of water, which accelerates the limiting step of the liberation of the $P_i$ by the enzyme.

MATLIN et al. (Biochemistry, 1992, 31, 8196–8200) have studied other mutations at position 153 of the *E. coli* alkaline phosphatase (replacement of the aspartic acid by alanine: D153A or by asparagine: D153N) and have also demonstrated that the presence of magnesium is essential for the activity of these mutants. Furthermore, while mutant D153N exhibits kinetic parameters which are similar to those of the wild-type enzyme, mutant D153A results in an increase in the $k_{cat}$ by a factor of 6.3, an increase in the $k_{cat}/K_m$ ratio (50 mM Tris, pH 8) by a factor 13.7 and an increase in the $K_i$ for $P_i$ (1M Tris, pH 8) by a factor of 159. Furthermore, the activity of this mutant increases by a factor of 25 when the pH is raised from 7 to 9.

The importance of the presence of magnesium for actually having a catalytic activity, both for mutant D153A and for mutant D153H, has been demonstrated by MURPHY et al. (J. Biol. Chem., 1993, 268, 29, 21497–21500), who show that mutation D153H results in the conversion of the magnesium-binding site into a zinc-binding site.

JANEWAY et al. have also explored the role of the residues in positions 153 and 328 of the *E. coli* alkaline phosphatase. Mutants D153H (replacement of the aspartic acid in position 153 by a histidine), K328H (replacement of the lysine in position 328 by a histidine) and D153H/K328H have been studied in particular, as have the interactions, within the active site of the alkaline phosphatase, involving water.

From this paper it emerges that:

mutant D153H exhibits a displacement of the optimum enzyme activity towards pH 10 and a decrease in affinity for magnesium; in the presence of additional magnesium, the catalytic activity is restored and is even greater than that of the wild-type enzyme.

Without doubt, this modification in activity is due to the fact that D153, in the wild-type enzyme, binds the magnesium by the mediation of two molecules of water; its elimination destabilizes the magnesium, which is replaced by a zinc (MURPHY et al., 1993, mentioned above) and yields an inactive form of the enzyme.

Nevertheless, the increase in the catalytic activity in the presence of magnesium is not clear; it might be due to an indirect effect on K328, which has no connection with D153.

Both MATLIN et al. (reference mentioned above) and JANEWAY et al. (reference mentioned above) demonstrate the essential role of magnesium in evaluating the enzyme activity of the alkaline phosphatase.

Mutant K328H/D153H exhibits the same behaviour as mutant D153H with regard to magnesium; furthermore, it exhibits a decreased $K_m$ and an increased $k_{cat}$.

This demonstrates the complexity of the action and the difficulty involved in assessing the interest of a mutant.

MURPHY et al. (Molecular Microbiology, 1994, 12, 3, 351–357) also summarize the properties of mutants D153H, K328H and D153H/K328H and arrive at the same conclusions as the various authors mentioned above.

In conclusion, mutants K328H or D153H exhibit a moderate increase in specific activity. While the double mutant (D153H/K328H) is more active than the single mutants, its thermal stability is not as great as that of the wild-type enzyme and the presence of magnesium is essential for expressing a high level of activity; furthermore, this double mutant D153H/K328H exhibits an increase in the $K_m$ by a factor which is greater than 30, resulting in a decrease in the $k_{cat}/K_m$ ratio (low affinity for the substrate).

Despite the fact that the His residues in positions 153 and/or 328 are involved in the higher performance of CIP, their presence itself is not sufficient to confer the desired characteristics on BAP, in order to obtain an effective and stable diagnostic tool, that is simultaneously possessing:

a catalytic activity (hydrolysis) of the order of that of mammalian alkaline phosphatase (CIP in particular), a high affinity for the phosphorus-containing substrate, and a high degree of thermal stability, that is of the order of that of the wild-type BAP.

Accordingly, the object set by the applicant has been to provide modified bacterial alkaline phosphatases which meet practical requirements more satisfactorily than do the alkaline phosphatases of the prior art.

The present invention relates to a modified alkaline phosphatase of bacterial origin, characterized in that it consists of a sequence of bacterial alkaline phosphatase (BAP) in which at least one of the amino acid residues in position 329 or in position 330 is replaced by another amino acid residue, which modified alkaline phosphatase exhibits a catalytic activity and an affinity for the substrate which are significantly increased (improved enzyme activity) as compared with the said activities of the corresponding wild-type bacterial alkaline phosphatase and a thermal stability which is of the order of that of the said wild-type bacterial alkaline phosphatase.

Within the meaning of the present invention, amino acid residue is understood to mean any natural amino acid residue and in particular: Ala, Cys, Asp, Glu, Phe, Gly, His, Ile, Lys, Leu, Met, Asn, Pro, Gln, Arg, Ser, Thr, Val, Trp or Tyr.

A modified alkaline phosphatase of bacterial origin (BAPm) is understood to mean a biologically active alkaline phosphatase whose mutations do not necessarily correspond to the amino acid residues of mammalian alkaline phosphatase (CIP, for example), which BAPm can, in particular, be obtained, by random or site-direct mutagenesis, from a chimeric alkaline phosphatase, that is a bacterial alkaline phosphatase which contains at least two amino acid residues from a mammalian alkaline phosphatase, in particular from calf intestinal alkaline phosphatase (CIP), and which is biologically inactive.

An enzyme exhibiting an improved enzyme activity is understood to mean an enzyme which exhibits an increased $k_{cat}$ and/or a decreased $K_m$ as compared with an unmodified enzyme.

In accordance with one advantageous embodiment of the said modified bacterial alkaline phosphatase, the phosphatase additionally contains a substitution at the level of amino acid residue 153 and/or of amino acid residue 328.

In accordance with another advantageous embodiment of the said modified bacterial alkaline phosphatase, the substitution at position 330 is preferably the replacement of an aspartic acid ($Asp^{330}$ or D) by an asparagine (Asn or N), an alanine (Ala or A) or a leucine (Leu or L).

In accordance with another advantageous embodiment of the said modified alkaline phosphatase, the substitution at position 329 is preferably the replacement of a glutamine ($Gln^{329}$ or Q) by an alanine (Ala or A).

In accordance with the invention, the said modified alkaline phosphatase also contains a histidine (His or H) in position 153 in place of an aspartic acid ($Asp^{153}$) and/or a histidine in position 328 in place of a lysine (Lys or K).

In accordance with the invention, the preferred mutants are selected from among:

mutant D330N, mutant D153H/D330N, mutant K328H/D330N, mutant D153H/K328H/D330N, mutant D330A, mutant D330L, mutant D153H/D330A, mutant D153H/D330L, mutant K328H/D330A, mutant K328H/D330L, mutant D153H/K328H/D330A, mutant D153H/K328H/D330L, mutant Q329A, mutant D153H/Q329A, mutant K328H/Q329A and mutant D153H/K328H/Q329A.

Also in accordance with the invention, the bacterial alkaline phosphatase sequence is preferably derived from *Escherichia coli* or from *Bacillus subtilis*.

According to another advantageous embodiment of the said modified bacterial alkaline phosphatase, the phosphatase contains, in addition to at least one of the substitutions such as defined above, at least one additional amino acid which is inserted between amino acids +6 and +7 of the said bacterial alkaline phosphatase.

One of these modified sequences which may be cited is SEQ ID No. 2:

```
                              6                               7
Arg Thr Pro Glu Met Pro Val Asp Phe Ser Arg Arg Ala Pro Gly Val
 1               5                  10                  15

Leu Glu Asn Arg Ala Ala Gln Gly Asp Ile Thr Ala Pro Gly Gly Ala
             20                  25                  30

Arg Arg Leu Thr Gly Asp Gln Thr Ala Ala Leu Arg Asp Ser Leu Ser
         35                  40                  45

Asp Lys Pro Ala Lys Asn Ile Ile Leu Leu Ile Gly Asp Gly Met Gly
     50                  55                  60

Asp Ser Glu Ile Thr Ala Ala Arg Asn Tyr Ala Glu Gly Ala Gly Gly
 65                      70                  75                  80

Phe Phe Lys Gly Ile Asp Ala Leu Pro Leu Thr Gly Gln Tyr Thr His
                 85                  90                  95

Tyr Ala Leu Asn Lys Lys Thr Gly Lys Pro Asp Tyr Val Thr Asp Ser
             100                 105                 110

Ala Ala Ser Ala Thr Ala Trp Ser Thr Gly Val Lys Thr Tyr Asn Gly
         115                 120                 125

Ala Leu Gly Val Asp Ile His Glu Lys Asp His Pro Thr Ile Leu Glu
     130                     135                 140

Met Ala Lys Ala Ala Gly Leu Ala Thr Gly Asn Val Ser Thr Ala Glu
145                     150                 155                 160

153
Leu Gln His Ala Thr Pro Ala Ala Leu Val Ala His Val Thr Ser Arg
                 165                 170                 175

Lys Cys Tyr Gly Pro Ser Ala Thr Ser Glu Lys Cys Pro Gly Asn Ala
             180                 185                 190

Leu Glu Lys Gly Gly Lys Gly Ser Ile Thr Glu Gln Leu Leu Asn Ala
         195                 200                 205

Arg Ala Asp Val Thr Leu Gly Gly Gly Ala Lys Thr Phe Ala Glu Thr
     210                 215                 220

Ala Thr Ala Gly Glu Trp Gln Gly Lys Thr Leu Arg Glu Gln Ala Gln
225                 230                 235                 240
```

-continued

| | | | | | | | | | | | | | |
|---|---|---|---|---|---|---|---|---|---|---|---|---|---|
| Ala | Arg | Gly | Tyr | Gln | Leu | Val | Ser | Asp | Ala | Ala | Ser | Leu | Asn | Ser | Val |
| | | | | 245 | | | | 250 | | | | 255 | | |
| Thr | Glu | Ala | Asn | Gln | Gln | Lys | Pro | Leu | Leu | Gly | Leu | Phe | Ala | Asp | Gly |
| | | | 260 | | | | | 265 | | | | | 270 | | |
| Asn | Met | Pro | Val | Arg | Trp | Leu | Gly | Pro | Lys | Ala | Thr | Tyr | His | Gly | Asn |
| | | 275 | | | | | 280 | | | | | 285 | | | |
| Ile | Asp | Lys | Pro | Ala | Val | Thr | Cys | Thr | Pro | Asn | Pro | Gln | Arg | Asn | Asp |
| | 290 | | | | | 295 | | | | 300 | | | | | |
| Ser | Val | Pro | Thr | Leu | Ala | Gln | Met | Thr | Asp | Lys | Ala | Ile | Glu | Leu | Leu |
| 305 | | | | | 310 | | | | | 315 | | | | | 320 |
| Ser | Lys | Asn | Glu | Lys | Gly | Phe | Phe | Leu | Gln | Val | Glu | Gly | Ala | Ser | Ile |
| | | | | 325 | | | | | 330 | | | | | 335 | |
| | | 328 | | 330 | | | | | | | | | | | |
| Asp | His | Gln | Asn | His | Ala | Ala | Asn | Pro | Cys | Gly | Gln | Ile | Gly | Glu | Thr |
| | | | 340 | | | | | 345 | | | | | 350 | | |
| Val | Asp | Leu | Asp | Glu | Ala | Val | Gln | Arg | Ala | Leu | Glu | Phe | Ala | Lys | Lys |
| | | 355 | | | | | 360 | | | | | 365 | | | |
| Glu | Gly | Asn | Thr | Leu | Val | Ile | Val | Thr | Ala | Asp | His | Ala | His | Ala | Ser |
| | 370 | | | | | 375 | | | | | 380 | | | | |
| Gln | Ile | Val | Ala | Pro | Asp | Thr | Lys | Ala | Pro | Gly | Leu | Thr | Gln | Ala | Leu |
| 385 | | | | | 390 | | | | | 395 | | | | | 400 |
| Asn | Thr | Lys | Asp | Gly | Ala | Val | Met | Val | Met | Ser | Tyr | Gly | Asn | Ser | Glu |
| | | | | 405 | | | | | 410 | | | | | 415 | |
| Glu | Asp | Ser | Gln | Glu | His | Thr | Gly | Ser | Gln | Leu | Arg | Ile | Ala | Ala | Tyr |
| | | | 420 | | | | | 425 | | | | | 430 | | |
| Gly | Pro | His | Ala | Ala | Asn | Val | Val | Gly | Leu | Thr | Asp | Gln | Thr | Asp | Leu |
| | | 435 | | | | | 440 | | | | | 445 | | | |
| Phe | Tyr | Thr | Met | Lys | Ala | Ala | Leu | Gly | Leu | Lys | * | | | | |
| 450 | | | | | 455 | | | | | 460 | | | | | |

In this sequence SEQ ID No. 2, the underlined fragment corresponds to the amino acids which are added between the proline and the valine, in positions 6 and 7, respectively, in the wild-type alkaline phosphatase from *E. coli*; the amino acids in bold letters correspond to the modified amino acids and the numbers in italics correspond to the positions of the equivalent amino acids in the wild-type alkaline phosphatase from *E. coli*.

Although the above sequence corresponds to mutant D153H/K328H/D330N, the invention nevertheless also includes the sequences corresponding to mutant s D330N, D153H/D330N and K328H/D330N, as well as the other mutants mentioned above.

Surprisingly, BAPs which are modified as specified above exhibit, at one and the same time:

improved catalytic properties (in particular improvement of the affinity of the enzyme for the substrate) which are suitable for permitting a decrease in the visualization time during its use in an assay test by up to a factor of 6 as compared with the reagent exhibiting the initial bacterial sequence and/or for increasing the sensitivity of this test, and a thermal stability of the order of that of the wild-type bacterial sequence (BAP).

The present invention also relates to nucleic acid sequences encoding any one of the proteins such as defined above.

Those of the said sequences which may be mentioned are:

the modified sequences which are obtained from the wild-type sequence, and modified sequences which include 27 additional bases between bases 18 and 19, that is between the codon encoding the proline in position 6 of the wild-type alkaline phosphatase and the codon encoding the valine in position 7, in accordance with SEQ ID No. 1:

| GTGAAACAAA | GCACTATTGC | ACTGGCACTC | TTACCGTTAC | TGTTTACCCC | TGTGACAAAA | 60 |
|---|---|---|---|---|---|---|

| GCC | CGG | ACA | CCA | GAA | ATG | CCC | GTC | GAC | TTC | AGT | CGA | CGA | GCT | CCC | GGG | 108 |
|---|---|---|---|---|---|---|---|---|---|---|---|---|---|---|---|---|
| Ala | Arg | Thr | Pro | Glu | Met | Pro | Val | Asp | Phe | Ser | Arg | Arg | Ala | Pro | Gly | |
| | | | | | 5 | | | | | 10 | | | | | 15 | |

| GTT | CTG | GAA | AAC | CGG | GCT | GCT | CAG | GGC | GAT | ATT | ACT | GCA | CCC | GGC | GGT | 156 |
|---|---|---|---|---|---|---|---|---|---|---|---|---|---|---|---|---|
| Val | Leu | Glu | Asn | Arg | Ala | Ala | Gln | Gly | Asp | Ile | Thr | Ala | Pro | Gly | Gly | |
| | | | | 20 | | | | | 25 | | | | | 30 | | |

```
GCT CGC CGT TTA ACG GGT GAT CAG ACT GCC GCT CTG CGT GAT TCT CTT    204
Ala Arg Arg Leu Thr Gly Asp Gln Thr Ala Ala Leu Arg Asp Ser Leu
            35              40                      45

AGC GAT AAA CCT GCA AAA AAT ATT ATT TTG CTG ATT GGC GAT GGG ATG    252
Ser Asp Lys Pro Ala Lys Asn Ile Ile Leu Leu Ile Gly Asp Gly Met
        50              55                      60

GGG GAC TCG GAA ATT ACT GCC GCA CGT AAT TAT GCC GAA GGT GCG GGC    300
Gly Asp Ser Glu Ile Thr Ala Ala Arg Asn Tyr Ala Glu Gly Ala Gly
    65              70                      75

GGC TTT TTT AAA GGT ATA GAT GCC TTA CCG CTT ACC GGG CAA TAC ACT    348
Gly Phe Phe Lys Gly Ile Asp Ala Leu Pro Leu Thr Gly Gln Tyr Thr
80              85                      90                      95

CAC TAT GCG CTG AAT AAA AAA ACC GGC AAA CCG GAC TAC GTC ACC GAC    396
His Tyr Ala Leu Asn Lys Lys Thr Gly Lys Pro Asp Tyr Val Thr Asp
                100             105                     110

TCG GCT GCA TCA GCA ACC GCC TGG TCA ACC GGT GTC AAA ACC TAT AAC    444
Ser Ala Ala Ser Ala Thr Ala Trp Ser Thr Gly Val Lys Thr Tyr Asn
            115             120                     125

GGC GCG CTG GGC GTC GAT ATT CAC GAA AAA GAT CAC CCA ACG ATT CTG    492
Gly Ala Leu Gly Val Asp Ile His Glu Lys Asp His Pro Thr Ile Leu
            130             135                     140

GAA ATG GCA AAA GCC GCA GGT CTG GCG ACC GGT AAC GTT TCT ACC GCA    540
Glu Met Ala Lys Ala Ala Gly Leu Ala Thr Gly Asn Val Ser Thr Ala
145             150                     155

153
GAG TTG CAG CAC GCC ACG CCC GCT GCG CTG GTC GCA CAT GTG ACC TCG    588
Glu Leu Gln His Ala Thr Pro Ala Ala Leu Val Ala His Val Thr Ser
160             165                     170                     175

CGC AAA TGC TAC GGT CCG AGC GCG ACC AGT GAA AAA TGT CCG GGT AAC    636
Arg Lys Cys Tyr Gly Pro Ser Ala Thr Ser Glu Lys Cys Pro Gly Asn
                180                     185                     190

GCT CTG GAA AAA GGC GGA AAA GGA TCG ATT ACC GAA CAG CTG CTT AAC    684
Ala Leu Glu Lys Gly Gly Lys Gly Ser Ile Thr Glu Gln Leu Leu Asn
            195                     200                     205

GCT CGT GCC GAC GTT ACG CTT GGC GGC GGC GCA AAA ACC TTT GCT GAA    732
Ala Arg Ala Asp Val Thr Leu Gly Gly Gly Ala Lys Thr Phe Ala Glu
        210                     215                     220

ACG GCA ACC GCT GGT GAA TGG CAG GGA AAA ACG CTG CGT GAA CAG GCA    780
Thr Ala Thr Ala Gly Glu Trp Gln Gly Lys Thr Leu Arg Glu Gln Ala
225                     230                     235

CAG GCG CGT GGT TAT CAG TTG GTG AGC GAT GCT GCC TCA CTG AAT TCG    828
Gln Ala Arg Gly Tyr Gln Leu Val Ser Asp Ala Ala Ser Leu Asn Ser
240                     245                     250                     255

GTG ACG GAA GCG AAT CAG CAA AAA CCC CTG CTT GGC CTG TTT GCT GAC    876
Val Thr Glu Ala Asn Gln Gln Lys Pro Leu Leu Gly Leu Phe Ala Asp
                260                     265                     270

GGC AAT ATG CCA GTG CGC TGG CTA GGA CCG AAA GCA ACG TAC CAT GGC    924
Gly Asn Met Pro Val Arg Trp Leu Gly Pro Lys Ala Thr Tyr His Gly
            275                     280                     285

AAT ATC GAT AAG CCC GCA GTC ACC TGT ACG CCA AAT CCG CAA CGT AAT    972
Asn Ile Asp Lys Pro Ala Val Thr Cys Thr Pro Asn Pro Gln Arg Asn
        290                     295                     300

GAC AGT GTA CCA ACC CTG GCG CAG ATG ACC GAC AAA GCC ATT GAA TTG   1020
Asp Ser Val Pro Thr Leu Ala Gln Met Thr Asp Lys Ala Ile Glu Leu
    305                     310                     315

TTG AGT AAA AAT GAG AAA GGC TTT TTC CTG CAA GTT GAA GGT GCG TCA   1068
Leu Ser Lys Asn Glu Lys Gly Phe Phe Leu Gln Val Glu Gly Ala Ser
320                     325                     330                     335

328         330
ATC GAT CAC CAG AAT CAT GCT GCG AAT CCT TGT GGG CAA ATT GGC GAG   1116
Ile Asp His Gln Asn His Ala Ala Asn Pro Cys Gly Gln Ile Gly Glu
                        340                     345                     350
```

| | | | | | | | | | | | | | | | | |
|---|---|---|---|---|---|---|---|---|---|---|---|---|---|---|---|---|
| ACG | GTC | GAT | CTC | GAT | GAA | GCC | GTA | CAA | CGG | GCG | CTG | GAA | TTC | GCT | AAA | 1164 |
| Thr | Val | Asp | Leu 355 | Asp | Glu | Ala | Val | Gln 360 | Arg | Ala | Leu | Glu | Phe 365 | Ala | Lys | |
| AAG | GAG | GGT | AAC | ACG | CTG | GTC | ATA | GTC | ACC | GCT | GAT | CAC | GCC | CAC | GCC | 1212 |
| Lys | Glu | Gly 370 | Asn | Thr | Leu | Val | Ile 375 | Val | Thr | Ala | Asp | His 380 | Ala | His | Ala | |
| AGC | CAG | ATT | GTT | GCG | CCG | GAT | ACC | AAA | GCT | CCG | GGC | CTC | ACC | CAG | GCG | 1260 |
| Ser | Gln 385 | Ile | Val | Ala | Pro | Asp 390 | Thr | Lys | Ala | Pro | Gly 395 | Leu | Thr | Gln | Ala | |
| CTA | AAT | ACC | AAA | GAT | GGC | GCA | GTG | ATG | GTG | ATG | AGT | TAC | GGG | AAC | TCC | 1308 |
| Leu 400 | Asn | Thr | Lys | Asp | Gly 405 | Ala | Val | Met | Val | Met 410 | Ser | Tyr | Gly | Asn | Ser 415 | |
| GAA | GAG | GAT | TCA | CAA | GAA | CAT | ACC | GGC | AGT | CAG | TTG | CGT | ATT | GCG | GCG | 1356 |
| Glu | Glu | Asp | Ser | Gln 420 | Glu | His | Thr | Gly | Ser 425 | Gln | Leu | Arg | Ile | Ala 430 | Ala | |
| TAT | GGC | CCG | CAT | GCC | GCC | AAT | GTT | GTT | GGA | CTG | ACC | GAC | CAG | ACC | GAT | 1404 |
| Tyr | Gly | Pro | His 435 | Ala | Ala | Asn | Val | Val 440 | Gly | Leu | Thr | Asp | Gln 445 | Thr | Asp | |
| CTC | TTC | TAC | ACC | ATG | AAA | GCC | GCT | CTG | GGG | CTG | AAA | TAA | | | | 1443 |
| Leu | Phe | Tyr 450 | Thr | Met | Lys | Ala | Ala 455 | Leu | Gly | Leu | Lys | | | | | |

In this sequence SEQ ID No. 1, the underlined fragment corresponds to the bases which are added between the proline codon and the valine codon; the sequences in bold letters correspond to the mutated codons and the numbers in italics correspond to the positions of the equivalent amino acids in the wild-type alkaline phosphatase from *E. coli*.

Although the above sequence encodes mutant D153H/K328H/D330N, the invention nevertheless also includes the sequences encoding mutant D330N, mutant D153H/D330N and mutant K328H/D330N, as well as the other mutants mentioned above.

The present invention also relates to a recombinant plasmid which is characterized in that it contains a nucleic acid sequence encoding a modified alkaline phosphatase in accordance with the invention and is suitable for expressing the said protein in an appropriate host cell.

In accordance with the invention, the said plasmid advantageously contains sequences which regulate the expression of the nucleic acid sequence encoding the modified alkaline phosphatase.

Regulatory sequences are understood to mean active sequences of the promoter and terminator type; those which may be mentioned, by way of example, are the promoter of the alkaline phosphatase gene (phoA promoter) or else the tac promoter, associated with the lacI$^Q$ repressor (Carrier et al., J. Immunol. Methods, 1995, 177–186 and Szmelcman et al., J. Acquired Immune Defic. Syndr., 1990, 3, 859).

The present invention also relates to a host cell which is transformed with a plasmid according to the invention, in particular a bacterium such as *E. coli*, the said host cell either being deficient for the chromosomal gene for alkaline phosphatase or else not expressing the chromosomal gene for alkaline phosphatase under the conditions in which the alkaline phosphatase gene carried by the plasmid according to the invention is expressed.

The present invention also relates to a method for selecting a modified bacterial alkaline phosphatase possessing both a catalytic activity which is improved as compared with that of the native bacterial alkaline phosphatase and a thermal stability of the order of that of the said native alkaline phosphatase, characterized in that it comprises:

i) preparing an inactive chimeric alkaline phosphatase, comprising the introduction, into the sequence encoding the BAP, of at least two codons encoding two amino acid residues from a mammalian alkaline phosphatase (CIP, in particular);

ii) carrying out a random or site-directed mutagenesis on the gene encoding this inactive chimeric alkaline phosphatase;

iii) expressing the alkaline phosphatases obtained in ii);

iv) selecting the bacterial clones expressing an alkaline phosphatase whose enzyme activity is restored; and v) sequencing the modified alkaline phosphatases thus obtained and selecting the compatibility mutation(s) to be introduced into a wild-type bacterial alkaline phosphatase in order to construct the said active modified bacterial alkaline phosphatase possessing the improved properties such as specified above (catalytic activity which is increased as compared with that of the native bacterial alkaline phosphatase and a thermal stability of the order of that of the said native alkaline phosphatase).

Step iv) makes it possible to obtain alkaline phosphatases which are termed revertants, that is phosphatases whose enzyme activity is restored as compared with the product of step i).

By way of example, the mutant obtained at step i) is, for example, mutant D153H/K328H/Q329G/D330H, corresponding to an inactive chimeric alkaline phosphatase, and the mutant obtained at step iv) is, for example, mutant D153H/K328H/Q329G/D330N, mutant D153H/K328H/Q329A/D330H, mutant D153H/K328H/Q329G/D330A or mutant D153H/K328H/Q329G/D330L, which are revertant enzymes, that is enzymes which are biologically active.

The mutations which are the cause of this phenotypic reversion are termed compatibility mutations because they enable two sequences of different origin to adapt to each other in order to form a modified protein which is biologically functional.

Step v) enables the said compatibility mutations to be selected so as to construct an active and thermally stable modified bacterial alkaline phosphatase which exhibits enzymic properties ($k_{cat}$ and/or $K_m$) which are improved as compared with the wild-type enzyme.

In accordance with this method, the said compatibility mutation [selected in steps iv) and v)] confers high-grade catalytic properties on a bacterial alkaline phosphatase/ mammalian alkaline phosphatase chimeric enzyme which is initially inactive. When transferred into the bacterial alkaline phosphatase, the effect of this mutation is to improve the catalytic properties of the enzyme. Finally, when associated with one of the other mutations as specified above, in particular with mutation D153H, it leads to an enzyme whose properties are close to those of the mammalian enzymes, while possessing a thermal stability which is close to that of the bacterial enzyme.

According to one advantageous embodiment of the invention, the mutations introduced at step i) at least concern the amino acid residues in positions 153, 328, 329 and 330 of the bacterial enzyme.

Preferably, they concern all the following residues:
residue 153: replacement of Asp by His,
residue 328: replacement of Lys by His,
residue 329: replacement of Gln by Gly,
residue 330: replacement of Asp by His.

Mutant D153H/K328H/Q329G/D330H (inactive chimeric alkaline phosphatase) is obtained, in particular.

According to another embodiment of the said method, the mutation which is introduced at step ii) at least concerns the amino acid residues in positions 329 and/or 330 of the bacterial enzyme and consists, in particular, of the replacement of His at 330 by Asn, by Ala or by Leu and/or consists of the replacement of Gly at position 329 by Ala; leading to the formation of the abovementioned biologically active revertants, namely: D153H/K328H/Q329G/D330N, D153H/K328H/Q329G/D330A, D153H/K328H/Q329G/D330L or D153H/K328H/Q329A/D330H.

The present invention also relates to a diagnostic reagent which is characterized in that it comprises an alkaline phosphatase which is modified in accordance with the invention.

The diagnostic reagent according to the invention may advantageously be prepared by conventional routes (chemical coupling) or by genetic manipulation, in particular employing a construct such as described in European patent applications No. 0 407 259 and No. 0 556 111.

The reagents according to the present invention are to be applied, in particular, in immunoenzymic assays; their advantages over the reagents which include the wild-type bacterial sequence of alkaline phosphatase are illustrated, for example, either by a reduction in the visualization time, by up to a factor of 6, and/or an increase in the sensitivity of the test, or by an increase in the signal.

In addition to the above provisions, the invention also includes other provisions which will be evident from the description which follows, which refers to exemplary embodiments of the method which is the subject-matter of the present invention, as well as to the attached drawings, in which:

FIG. 1 depicts the plasmid pLIP4.0.B, which is suitable for expressing the genes encoding a modified phosphatase, FIG. 2 depicts the nucleotide sequence of vector pLIP4.0.B, in which the coding sequence of the gene phoA is in bold, (SEQ ID No. 9)

Figure 3:
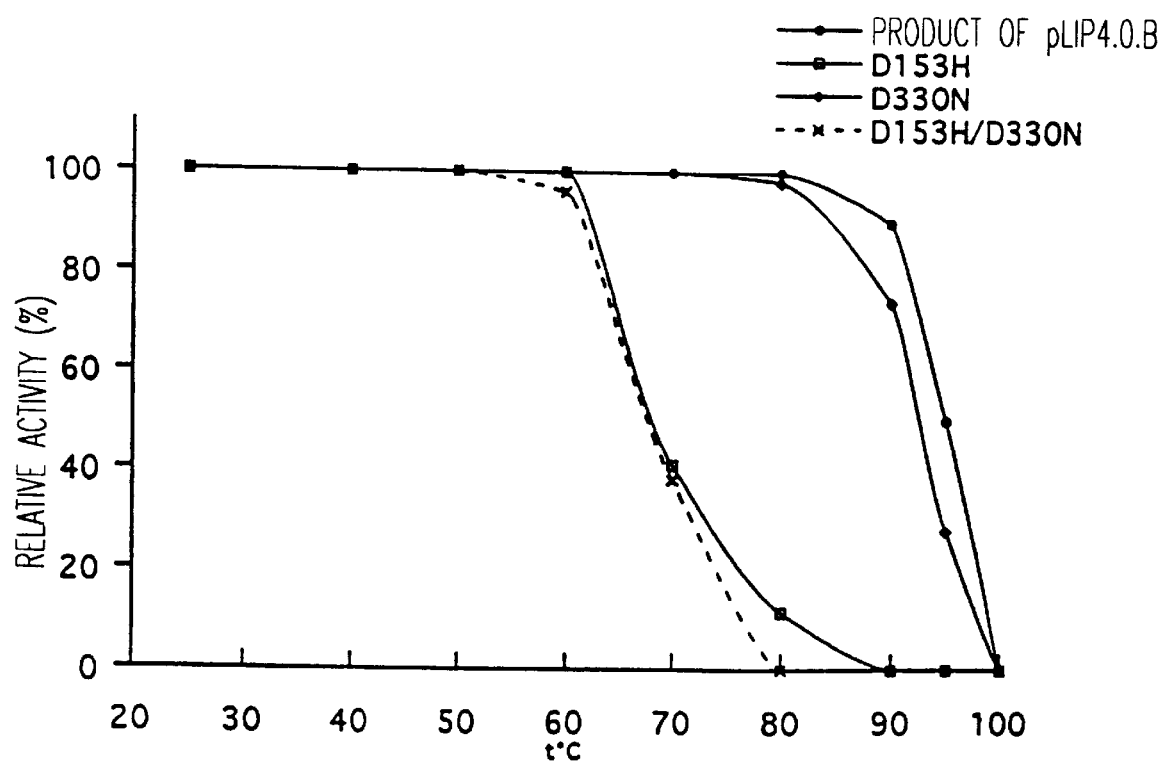
Figure 5A:
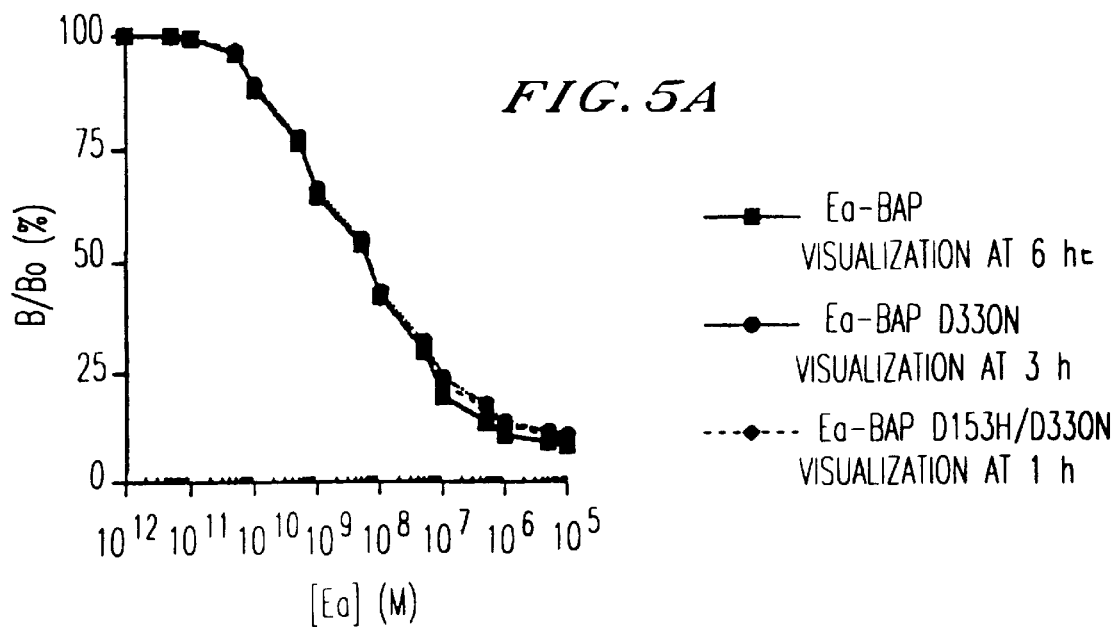
Figure 5B:
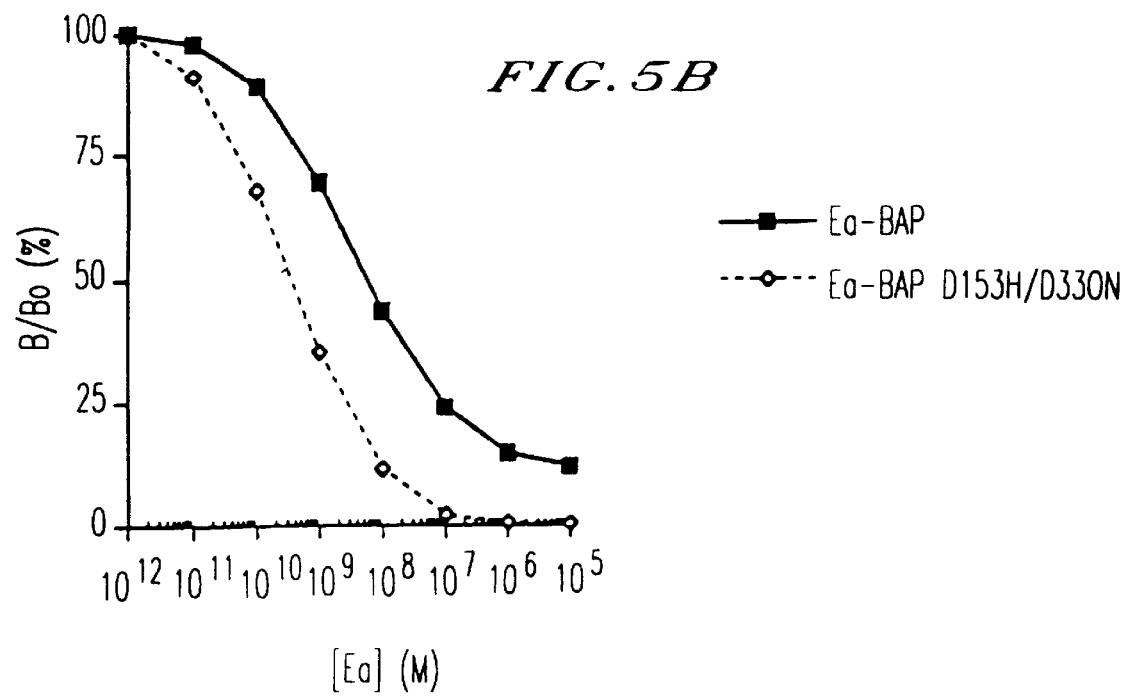

FIG. 3 illustrates the thermal stability of the various alkaline phosphatases which are produced, FIG. 4 illustrates the comparison of the enzyme activities of the various toxin/phosphatase tracers which are specifically attached to an anti-toxin antibody which is adsorbed onto a microtitration plate (measure of the specific binding, obtained by subtracting the non-specific binding from the total binding), FIGS. 5A and 5B illustrate the effect of the mutations on the visualization time and the sensitivity of a competitive immunoenzymic assay for toxin, FIG. 6 depicts the sequence of the inserted gene encoding proinsulin, (SEQ ID No. 10). Peptide C is depicted in bold: the bases which are added to the proinsulin sequence, and which enable both the proinsulin to be inserted into vector pLIP5 and the reading frame of the phoA gene to be restored, are in italics, and FIG. 7A depicts the comparison of the visualization times which are required for assaying insulin as a function of the tracer employed, and FIG. 7B illustrates the effect of the mutations on the sensitivity of a competitive immunoenzymic assay for insulin.

However, it is to be understood that these examples are provided by way of illustrating the subject-matter of the invention, of which they in no way constitute a limitation.

EXAMPLE 1

Construction of chimeric genes encoding a modified bacterial alkaline phosphatase.

These constructions were carried out by site-directed mutagenesis (KUNKEL et al., Methods Enzymol., 1987, 154, 367–382), on a derivative of the natural gene for bacterial alkaline phosphatase.

The initial vector is plasmid pLIP4.0 (GILLET et al., Analytical Chemistry, 1993, 65, 1779–1784), which is a derivative of the plasmid pJC2431, possessing the wild-type gene of bacterial alkaline phosphatase (LAZZARONI et al., J. Bacteriol., 1985, 164, 1376–1380). It contains the gene for alkaline phosphatase, which gene is modified in its 5'-coding part by the insertion of several restriction sites for allowing a foreign gene to be integrated.

Furthermore, a BamHI restriction site has been introduced, by site-directed mutagenesis, into this vector, upstream of the Shine-Dalgarno sequence of the phoA gene. The oligonucleotide which is used for this experiment is the following:

TGTACAAATACATTAAAGGATCCAAA-CAAAGCGACTAT (SEQ ID No. 3) (the BamHI site is indicated in bold in the sequence).

The phoA promoter, flanked by the Eco0109 I or HindIII and BamHI sites, can thus be changed at will. The resulting vector is designated pLIP4.0.B (FIG. 1: diagrammatic representation of vector pLIP4.0.B, and FIG. 2: nucleotide sequence of vector pLIP4.0.B).

Three mutations have been simultaneously introduced into the gene for E. coli alkaline phosphatase in order to replace residues 328, 329 and 330 of the bacterial enzyme by the equivalent residues which are present in the mammalian phosphatases. This experiment was carried out on a SacI/SphI fragment of the gene for the phosphatase (phoA), inserted into an M13 phage, using the following synthetic oligonucleotide:

GATTCGCAGCATGATGACCGTGATCGATTGACGC (SEQ ID No. 4) (the modified sequence is indicated in bold).

The mutated fragment was then reinserted into vector pLIP4.0.B and the nucleic acid sequence was checked once again. The D153H mutation was independently constructed in accordance with an identical protocol, using an appropriate oligonucleotide, and added by means of genetic recombination to the three previous mutations. The following quadruple mutant is obtained: D153H/K328H/Q329G/D330H. The first letter indicates the residue which is initially present in the bacterial alkaline phosphatase, the number corresponds to the position of the residue in the wild-type bacterial sequence, and the second letter represents the mutation which is introduced and which corresponds to the amino acid which is present in the mammalian phosphatases.

EXAMPLE 2

Production, purification and enzymic characteristics of the chimeric alkaline phosphatases.

The different gene constructs described in Example 1, as well as vector pJC2431, containing the wild-type gene for bacterial alkaline phosphatase, were introduced into the strain E. coli CC118, which is deficient for the chromosomal gene for alkaline phosphatase (MANOIL and BECKWITH, P.N.A.S., 1985, 85, 8129–8131).

The bacterial clones were cultured on a medium which contained the substrate 5-bromo-4-chloro-3-indolyl phosphate. Alkaline phosphatase-expressing colonies which possess a sufficiently. high specific activity hydrolyse the substrate and appear blue. This is the case for bacteria which harbour plasmids pJC2431 and pLIP4.0.B. By contrast, the clone which has integrated plasmid pLIP4.0.B-D153H/K328H/Q329G/D330H is white and appears incapable of hydrolysing the colorimetric substrate. The protein which is produced therefore lacks enzyme activity.

The various alkaline phosphatases are purified from 200 ml of bacterial culture. The periplasmic proteins are extracted by osmotic shock (NEU and HEPPEL., J. Biol. Chem., 1965, 240, 3685–3692) and then concentrated 20-fold and dialysed against a 20 mM Tris-HCl, pH 8, 1 mM $MgCl_2$ buffer using a Centricon® 30 membrane. The proteins are separated by isoelectric focusing on a Mono P HR® 5/5 Pharmacia column.

The different alkaline phosphatases are then is isolated from the buffer components on a molecular sieve (Pharmacia G-75) and stored in a medium containing 10 mM $MgCl_2$. The purity of the proteins which have been obtained is monitored on an SDS/polyacrylamide gel.

The electrophoretic mobility which is observed is identical for all the proteins produced from the vectors which are derived from pLIP4. It is less than that obtained for a commercial alkaline phosphatase (Sigma) or produced from the wild-type gene contained in vector pJC2431. This difference corresponds to approximately 1000 da. It is in agreement with the presence of the 9 additional amino acids which are contained in the N-terminal part of the phosphatases which are specified by the vectors which are derived from pLIP4. These residues correspond to the additional restriction sites introduced into the gene of the pLIP4 vectors. A scanning measurement demonstrates that this band constitutes more than 95% of the stained proteins on the gel.

The kinetic constants ($k_{cat}$ and $K_m$) of the enzymes were measured using para-nitrophenyl phosphate (pNPP) as substrate, at 25° C. in a 1M Tris-HCl, pH 8.0, buffer, and measuring the liberation of p-nitrophenolate at 410 nm, as illustrated in Table I below, under the following conditions: preincubation in 1M Tris-HCl, pH 8.0, 10 mM $Mg^{2+}$; reaction in 1M Tris-HCl, pH 8.0.

TABLE I

|  | $k_{cat}$ (s$^{-1}$) | $K_m(\mu M)$ | $k_{cat}/K_m$ (10$^6$M$^{-1}$.s$^{-1}$) |
| --- | --- | --- | --- |
| pJC2431 | 65 ± 1 | 23 ± 0.1 | 2.8 |
| pLIP4.0.B | 78 ± 4 | 30 ± 5 | 2.6 |
| D153H/K328H/Q329G/D330H | <0.7 | ND | ND |

The values for $k_{cat}$ and $K_m$ were obtained from the graphical plot of Eadie and Hofstee (vi=f(vi/[s])) (L. PENASSEd, Les enzymes: cinétique et mecanismes d'action (the enzymes: kinetics and mechanisms of action), MASSON and CIE, eds., 1974) and calculated using the KALEIDAGRAPH® software (published by Synergy Software). The enzyme obtained from plasmid pLIP4.0.B exhibits kinetic parameters which are similar to those of the wild-type enzyme. The presence of an insertion in the N-terminal region of the protein does not, therefore, significantly modify the catalytic activity of the enzyme.

The addition of the D153H mutation to these modifications renders the enzyme completely silent, while it continues to be produced normally by the bacterium. Thus, the introduction of 4 residues of mammalian origin into the bacterial alkaline phosphatase is not compatible with the maintenance of an enzymically functional form. The presence of only two of them, mutations D153H and K328H, has a limited effect on the enzymic properties (JANEWAY et al., Biochemistry, 1993, 32, 1601–1609). The 328–330 loop, and more specifically residues 329 and 330, therefore play an important role in the observed loss of activity.

EXAMPLE 3

Random mutagenesis on the inactive chimera, selection of phenotypic revertants and identification of the mutations which are the cause of this reversion.

A random mutagenesis is carried out on the SacI/SphI portion of the quadruple mutant of alkaline phosphatase using the PCR (polymerase chain reaction) technique (SAIKI et al., Science, 1988, 239, 487–491).

The experiment is carried out using Taq polymerase (BRL), which, on average, makes one error per 30,000 nucleotides incorporated, and the following oligonucleotides:

AACAACATTGGCGGCATGCGGGCC (the SphI site is in bold in the sequence) (SEQ ID No. 5)

GACTTCAGTCGACGAGCTCCCGGG (the SacI site is in bold in the sequence). (SEQ ID No. 6)

The number of amplification cycles is 30. The gene fragment obtained is monitored on an agarose gel and purified on Sephaglass® (Pharmacia). It is then digested with the enzymes SacI and SphI and then reinserted into the original plasmid in place of the non-mutagenized SacI/SphI fragment.

CC118 bacteria are transformed with the ligation product by means of electroporation (Biorad system) and the clones are spread on alkaline phosphatase-inducing medium which contains ampicillin and a colorimetric substrate for the enzyme, 5-bromo-4-chloro-3-indolyl phosphate, whose hydrolysis results in a blue product.

Two blue clones were obtained per 50,000 white ones. The cause of this phenotypic reversion was sought by sequencing the corresponding genes. It reveals the presence of one and the same mutation, H330N, in both these clones. This type of mutation has been termed a compatibility mutation by virtue of its property of rendering compatible the presence, on one and the same gene, of residues which belong to two phosphatases of different origin, initially giving rise to an enzyme which lacks catalytic activity.

EXAMPLE 4

Enzymic properties of the alkaline phosphatase produced by the revertant clone (vector pLIP4.0.B.-D153H/K328H/Q329G/H330N).

The alkaline phosphatase which was synthesized by the clone selected in Example 3 was purified using the procedure described in Example 2, and its catalytic properties were measured at pH 8, as illustrated in Table II below, under the following conditions: preincubation in 1M Tris-HCl, pH 8.0, 10 mM $Mg^{2+}$; reaction in 1M Tris-HCl, pH 8.0.

TABLE II

|  | $k_{cat}$ (s$^{-1}$) | $K_m$ ($\mu$M) | $k_{cat}/K_m$ (10$^6$M$^{-1}$.s$^{-1}$) |
|---|---|---|---|
| pLIP4.0.B | 78 ± 4 | 30 ± 5 | 2.6 |
| D153H/K328H/Q329G/H330N (revertant) | 82 ± 2 | 49 ± 6 | 1.7 |
| D330N | 148 ± 3 | 20 ± 2 | 7.2 |
| K328H | 78 ± 2 | 58 ± 2 | 1.3 |
| K328H/D330N | 53 ± 2 | 114 ± 9 | 0.5 |
| D153H | 110 ± 4 | 50 ± 5 | 2.2 |
| D153H/D330N | 215 ± 18 | 34 ± 7 | 6.4 |
| D153H/K328H/D330N | 160 ± 4 | 52 ± 6 | 3.1 |

The measured catalytic activity is similar to that of the wild-type bacterial enzyme. The affinity for the substrate is slightly decreased.

The compatibility mutation H330N (which does not correspond either to a natural residue of the enzyme or to a residue which is present in the mammalian enzymes) is therefore capable of conferring high-grade catalytic properties on the mutated enzyme.

A check was also made to confirm that the presence of a 330D residue (residue present in the bacterial phosphatase) does not lead to a result of this nature.

EXAMPLE 5
Properties of the 330N mutation alone or in combination with the different mutations of mammalian type.

An evaluation was carried out of the impact of the 330N mutation, or of this mutation in combination with mutations D153H and/or K328H, in a wild-type bacterial alkaline phosphatase context.

In order to carry out this study, the D330N mutation was introduced by site-directed mutagenesis into the gene carried by vector pLIP4.0.B in its initial state or modified by D153H, K328H or D153H/K328H, also by means of site-directed muta-genesis.

The proteins were produced and purified as in Example 2.
The kinetic parameters wre determined at pH 8 and at pH 10 and are given in Table II above and Table III below.

As compared with the constants which were determined for the enzyme produced by vector pLIP4.0.B., the D330N mutation induces, at pH 8, an increase, by a factor of 2, in the catalytic velocity of the modified enzyme, associated with a 30% increase in the affinity for the substrate. In combination with the K328H mutation, the catalytic velocity falls below the level of that of the initial enzyme and the affinity for the substrate falls by a factor of from 3 to 4. While the K328H mutation does not, on its own, modify the catalytic velocity of the enzyme, it induces a decline, by a factor of 2, in the affinity. This latter result is in agreement with the studies published by JANEWAY et al., Biochemistry, 1993, 32, 1601–1609.

When associated with the D153H mutation, the D330N mutation unexpectedly induces an increase, by a factor of close to 3, in catalytic velocity and does not significantly modify the affinity for the substrate.

Under similar conditions, the D153H mutation on its own only increases the catalytic velocity 1.4-fold and decreases the affinity for the substrate by a factor of close to 2.

Finally, the catalytic velocity of the triple mutant D153H/K328H/D330N falls back to the level of that of mutant D330N on its own and induces a drop, by a factor of 2, in the affinity for the substrate.

This result is to be compared with those obtained with the double mutant D153H/K328H (JANEWAY et al., Biochemistry, 1993, 32, 1601–1609) which demonstrate a decrease, by a factor of 4, in the catalytic velocity, and of 3 in the affinity for the substrate, as compared with the wild-type enzyme.

At pH 10, the enzyme produced by plasmid pLIP4.0.B exhibits a catalytic velocity which is similar to that observed at pH 8 in 1M Tris and an affinity for the substrate which is diminished by a factor of 3, as illustrated in Table III below, under the following conditions: preincubation in 0.1M CAPS (cyclohexylaminopropanesulphonic acid), 0.4M NaCl, pH 10.0, 10 mM Mg$^{2+}$; reaction in 0.1M CAPS, 0.4M NaCl, pH 10.0, 10 mM Mg$^{2+}$.

TABLE III

|  | $k_{cat}$ (s$^{-1}$) | $K_m$ ($\mu$M) | $k_{cat}/K_m$ (10$^6$M$^{-1}$.s$^{-1}$) |
|---|---|---|---|
| pLIP4.0.B | 80 ± 3 | 90 ± 8 | 0.9 |
| D153H/K328H/Q329G/H330N (revertant) | 227 ± 4 | 562 ± 45 | 0.4 |
| D330N | 201 ± 10 | 47 ± 4 | 4.3 |
| K328H | 214 ± 11 | 105 ± 11 | 2.0 |
| K328H/D330N | 254 ± 20 | 112 ± 9 | 2.3 |
| D153H | 240 ± 12 | 320 ± 30 | 0.8 |
| D153H/D330N | 1389 ± 110 | 350 ± 30 | 4.0 |
| D153H/K328H/D330N | 650 ± 43 | 170 ± 16 | 3.8 |

This result is similar to that observed by JANEWAY et al., 1993, on the wild-type enzyme. In that case too, insertion of several amino acids N-terminally in the enzyme did not significantly modify its behaviour.

While the revertant clone possesses a catalytic activity which is increased by a factor of 3, its affinity for the substrate is decreased by a factor of 6. Mutant D330N possesses a catalytic velocity which is 2.5-fold greater than that of the non-mutated enzyme under the same conditions and an affinity which is elevated by a factor of 2.

Double mutant K328H/D330N exhibits an activity which is 3-fold greater and an affinity which is slightly diminished by approximately 20%. Double mutant D153H/D330N exhibits a catalytic velocity which is increased 17-fold as compared with the initial enzyme, 7-fold as compared with single mutant D330N and 6-fold as compared with single mutant D153H. In this case, there is a genuine synergistic effect between these two mutations, D153H/D330N. By contrast, the affinity for the substrate is decreased by a factor of approximately 4 as compared with the bacterial enzyme, and this drop can be attributed to the D153H mutation, which induces a similar effect on its own. The association of the three mutations, D153H/K328H/D330N, engenders a catalytic velocity and an affinity which are intermediate in value as compared with the values obtained for the two double mutants.

The combination D153H/D330N constitutes the most efficacious construct in terms of catalytic velocity, which reaches a value approaching that of CIP, whose $k_{cat}$ is of the order of 2000 s$^{-1}$.

The thermal stability of the enzymes produced by vector pLIP4.0.B and the D153H, D330N and D153H/D330N derivatives was measured (FIG. 3). The enzymes are preincubated at 25° C. for 2 h in a 1M Tris, pH 8, 100 mM Mg$^{++}$ buffer.

An aliquot is held at the indicated temperature for 15 min in a 1M Tris, pH 8, 10 mM Mg$^{++}$ buffer. Following cooling in ice, the enzyme activity is measured at 25° C. for 15 min in the presence of 5 mM of paranitrophenyl phosphate.

The proteins produced by vector pLIP4.0.B (curve -●-) and mutant D330N (curve -◇-) have a half-denaturation temperature of approximately 95° C., which is similar to that of the natural bacterial alkaline phosphatase. Neither the N-terminal insertion of several amino acids nor the D330N mutation induces an increase in the sensitivity of the enzyme to temperature. By contrast, mutant D153H (curve -□-) and double mutant D153H/D330N (-x-) have a half-denaturation temperature of approximately 70° C., which is similar to that published by JANEWAY et al., 1993, for mutant D153H. This value is markedly higher than the value published for CIP, which is in the vicinity of 55° C. or 65° C. in the presence of $Mg^{2+}$ (control conditions established for the example).

EXAMPLE 6
Construction of toxin/alkaline phosphatase mutant fusion vectors.

Vectors pLIP4.0.B, pLIP4.0.B/D330N and pLIP4.0.B/D153H/D330N were digested with the enzyme SalI and then reclosed on themselves in such a manner as to create a frame shift in the reading frame of the phoA gene. The CC118 bacteria which are transformed with these vectors appear white on PhoA-inducing medium containing ampicillin and the substrate 5-bromo-4-chloro-3-indolyl phosphate. These frame-shifted vectors are designated pLIP4.B, pLIP4.B/D330N, pLIP4.B/D153H/D330N.

A PCR reaction is carried out on the portion of the vector pLIP1 (GILLET et al., Protein Engineering, 1992, 5, 3, 273–278) which carries the gene encoding the snake venom toxin erabutoxin a, in such a manner as to introduce, at the ends of the gene, the SalI and XmaI sites which are required for cloning into the pLIP4 vectors. The following oligonucleotides are employed:

GAAATGCCCGTCGACAGGATATGTTTTAAC (the SalI site is in bold in the sequence), (SEQ ID No. 7)

GAACCCCGGGAGCTCCATTGTTGCAGACCT (the XmaI site is in bold in the sequence). (SEQ ID No. 8)

The number of amplification cycles is 30. The gene which is obtained is checked on a low melting point agarose gel and is extracted from the gel by treating with phenol and chloroform. It is then digested with the restriction enzymes SalI and XmaI and inserted into the double-stranded DNA of the phage M13mp18 for the purpose of checking the sequence.

The gene is then inserted between the SalI and XmaI sites of vectors pLIP4.B, pLIP4.B-D330N and pLIP4.B-D153H/D330N. CC118 bacteria are transformed with the ligation product and spread on alkaline phosphatase-inducing medium containing ampicillin and the substrate 5-bromo-4-chloro-3-indolyl phosphate.

The colonies expressing the erabutoxin a/alkaline phosphatase (Ea/PhoA) fusion protein hydrolyse the substrate and appear blue. 21 blue clones were obtained per 300 white clones in the case of the pLIP4.B/Ea construct, 4 blue clones per 100 white ones in the case of the pLIP4.B-D330N/Ea construct, and 4 blue clones per 113 white ones in the case of the pLIP4.B-D153H-D330N/Ea construct. The presence of the insert in the constructs was verified by SacI/XmaI restriction (insert of approximately 200 bp) and the sequence of the gene encoding Ea was once again verified by sequencing.

EXAMPLE 7
Production/extraction of immunoenzymic tracers.

Production of the different fusion proteins is carried out using 400 ml of bacterial culture. The periplasmic proteins are extracted by osmotic shock and then concentrated on a YM-30 AMICON membrane down to a volume of 1 ml and dialysed against a 20 mM Tris-HCl, pH 8, 10 mM $MgCl_2$ buffer in the case of the unmodified hybrid and mutant D330N; the buffer used in the case of mutant D153H/D330N is 20 mM Tris-HCl, pH 8, 100 mM $MgCl_2$. The solutions are stored at −20° C. in the presence of 0.02% $NaN_3$.

EXAMPLE 8
Comparison of the enzyme activities of the different erabutoxin-a/modified alkaline phosphatase tracers which are specifically attached to an anti-toxin antibody which is adsorbed onto a microtitration plate, and the effect of the mutations on the visualization time and the sensitivity of a competitive immunoenzymic assay for the toxin. 1) Enzyme activity:

The toxin-specific monoclonal antibody Mα2–3 (TREMEAU et al., FEBS Lett., 1986, 208, 236–240) is adsorbed, overnight at 40° C., onto a microtitration plate at the rate of 10 ng per well in a volume of 50 µl of 50 mM Tris-HCl, pH 7.4, buffer. The wells are then saturated, overnight at 4° C., with 250 µl of a 100 mM Tris-HCl, pH 7.4, solution containing 0.3% bovine serum albumin.

5 washings are carried out using a 10 mM Tris-HCl, pH 7.4, 0.05% Tween®2 buffer.

The different tracers are diluted in a 100 mM Tris-HCl, pH 7.4, 0.1% bovine serum albumin, 10 mM $MgCl_2$ buffer. 50 µl volumes of these solutions are added to the titration wells and the plates are incubated overnight at 4° C.

5 washings are carried out using a 10 mM Tris-HCl, pH 7.4, 0.05% Tween®2 buffer.

The quantity of tracer which is fixed to the plates is visualized by adding 200 µl of 1M Tris-HCl, pH 8, 10 mM $MgCl_2$, 10 mM para-nitrophenyl phosphate (pNPP) in the case of the unmodified tracer and that carrying the D330N mutation; 200 µl of 100 mM CAPS, pH 10.0, 400 mM NaCl, 10 mM $MgCl_2$, 10 mM pNPP buffer are employed in the case of the tracer carrying the two mutations, D153H/D330N. The optical density is measured at 410 nm after two and a half hours and after 24 hours of incubation at room temperature.

The same experiments are carried out in the presence of an excess of toxin (50 µl of a 1 mg/ml toxin solution) in order to measure the non-specific binding, which is subtracted from the total binding. The results are given in FIG. 4.

2) Effect of the mutations on the visualization time and the sensitivity:

Calibration curves are constructed using the microtitration plates prepared as in 1), employing the Mα2-3 antibody. The different tracers are employed at the same concentration and the erabutoxin is employed at varying concentrations ($10^{-5}$ to $10^{-12}$M) as a competitor. 200 µl of solution containing 10 mM pNPP substrate are added in a 1M Tris-HCl, pH 8, 10 mM $MgCl_2$ buffer in the case of the unmutated tracer and in the case of the tracer which is mutated in position D330N. The incubation is carried out in a 100 mM CAPS, pH 10, 400 mM NaCl, 10 mM $MgCl_2$ buffer in the case of the double mutant, D153H/D330N. The standard competition curves which are obtained are depicted in FIG. 5A.

In a second series of experiments, which is carried out in the same buffers as before, the concentration of the tracer containing the double mutation, D153H/D330N, is decreased by a factor of 16 in order to give the same signal (OD of 0.5 at 410 nm in 6 hours), in the absence of competitor, as the tracer which does not contain a mutation. Under these conditions, the quantity of toxin which is required in order to inhibit the enzymic signal by 50% is decreased by a factor of 17 when the tracer carrying the mutations is employed (0.4 nM instead of 7 nM). The results are depicted in FIG. 5B.

These results demonstrate that the visualization time of the assay is reduced by a factor of 2 in the case of mutant D330N and by a factor of 6 in the case of mutant D153H/D330N, and that the sensitivity of the assay (expressed as the concentration of antigen inhibiting 50% of the signal) is improved by a factor of 17 (in the case of the double mutant).

EXAMPLE 9

Construction of proinsulin/mutant alkaline phosphatase fusion vectors and production of immunoenzymic tracers.

A synthetic gene encoding human proinsulin was constructed and inserted into the SalI and SacI sites of the vector pLIPS (CARRIER et al., J.I.M., 1995, 181, 177–186), which is a derivative of vector pLIP4.B in which the phoA promoter has been replaced by the tac promoter associated with the $lacI^Q$ repressor. The sequence of the inserted gene encoding proinsulin is depicted in FIG. 6.

The D330N and D153H/D330N mutations were introduced into this vector by genetic recombination between the pLIP4.0.B vectors carrying these mutations and the pLIP5/proinsulin vector.

The resulting constructs were verified by sequencing. The resulting plasmids were used to transform the *E. coli* strain W3110 (American Type Culture Collection No. 27325).

The different proinsulin/alkaline phosphatase tracers are produced using 400 ml of bacterial culture. The samples are treated as in Example 7.

EXAMPLE 10

Effect of the mutations on the visualization time and the sensitivity of a competitive immunoenzymatic assay for insulin.

1) Comparison of the visualization times:

First of all, the quantity of the different tracers was measured in insulin equivalents using a competitive commercial RIA test (INSI-PR kit) so as to standardize the tracer solutions employed in the following ELISA tests. The same quantity of tracer will thus be introduced into the different tests which are performed.

Goat anti-mouse immunoglobulin antibodies (IgG+IgM, H+L, Jackson ImmunoResearch Laboratories, Baltimore) were adsorbed onto microtitration plates, overnight at 4° C., in a 50 mM Tris-HCl, pH 7.4, buffer in an amount of 100 µl per well and at a concentration of 10 µg/ml. The wells are then saturated, overnight at 4° C., with 200 µl of a 100 mM Tris-HCl, pH 7.4, 0.3% bovine serum albumin solution. Following washings, which were carried out as in Example 8, 50 µl of a standardized solution of immunoenzymic tracer, 50 µl of differing concentrations of human insulin and then 50 µl of a solution of anti-insulin monoclonal antibody are added to the microtitration wells and incubated overnight at 4° C. The incubation buffer is 100 mM Tris-HCl, pH 7.4, 0.1% bovine serum albumin, 10 mM $MgCl_2$. The wells are washed and then 200 µl of buffer containing 10 mM pNPP substrate are added in a 1M Tris-HCl, pH 8, 10 mM $MgCl_2$ buffer in the case of the non-mutated tracer and in the case of the tracer which is mutated in position D330N, whereas, in the case of the D153H/D330N tracer, the incubation is carried out in a 100 mM CAPS, pH 10, 400 mM NaCl, 10 mM $MgCl_2$ buffer. The optical density at 410 nm is read when it reaches 0.5 in the absence of insulin. The results are depicted in FIG. 7A.

2) Effect of the mutations on the visualization time and the sensitivity of a competitive immunoenzymic assay for insulin:

In a second experiment, the concentration of the tracer carrying the double mutation, D153H/D330N, is decreased by a factor of 16 so as to obtain the same OD at 410 nm of 0.5 after 6 hours of visualization, in the absence of competitor, for the tracer carrying the mutations and for that without mutation. The experiments are carried out under the same conditions as before and the results are depicted in FIG. 7B. The concentration of insulin which is required in order to decrease the resulting signal by half is 4.5 times lower when the tracer carrying the mutations is employed than when the tracer without mutation is used (27 µU and 120 µU, respectively).

These results demonstrate that the visualization time of the assay is reduced by a factor of 2 in the case of the D330N mutant and by a factor of 6 in the case of the D153H/D33ON mutant, and that the sensitivity of the assay (expressed as the concentration of antigen inhibiting 50% of the signal) is improved by a factor of 4.5 (in the case of the double mutant).

EXAMPLE 11

Site-directed mutagenesis on the inactive chimera, in positions 329 and/or 330: selection of the biologically active revertants.

On carrying out a site-directed mutagenesis (KUNKEL et al., Methods Enzymol., 1987, 154, 367–382, cited above) on positions 329 and 330, respectively, starting with the inactive chimera according to Example 1, the following revertants are obtained:

D153H/K328H/Q329A/D330H

D153H/K328H/Q329G/D330A

D153H/K328H/Q329G/D330L which are biologically active and which, in particular, exhibit an improved affinity for the enzyme substrate.

As is evident from that which has been stated above, the invention is in no way limited to those of its modes of implementation, of realization and of application which have just been described more explicitly; on the contrary, it encompasses all the variants of these modes which can be conceived by the skilled person without departing from either the scope or range of the present invention.

---

What is claimed is:

1. A modified alkaline phosphatase of bacterial origin, comprising a wild-type bacterial alkaline phosphatase (BAP) sequence in which at least one of the amino acid residues in position 329 or in position 330 is replaced by another amino acid residue, which modified alkaline phosphatase exhibits at least a catalytic activity which is increased as compared with the catatytic activity of the corresponding wild-type bacterial alkaline phosphatase.

2. The modified alkaline phosphatase of bacterial origin according to claim 1, wherein amino acid residue 153 and/or amino acid residue 328 is substituted.

3. The modified alkaline phosphatase of bacterial origin according to claim 1, wherein the substitution at position 330 is the replacement of an aspartic acid ($Asp^{330}$ or D), by an asparagine (Asn or N), an alanine (Ala or A) or a leucine (Leu or L).

4. The modified alkaline phosphatase of bacterial origin according to claim 1, wherein the substitution at position 329 is the replacement of a glutamine ($Gln^{329}$ or Q) by an alanine (Ala or A).

5. The modified alkaline phosphatase of bacterial origin according to claim 2, wherein a histidine (His or H) is substituted in position 153 for an aspartic acid ($Asp^{153}$) and/or a histidine is substituted in position 328 for a lysine (Lys or K).

6. The modified alkaline phosphatase of bacterial origin according to claim 2, selected from the group consisting of mutant D330N, mutant D153H/D330N, mutant K328H/D330N mutant D153H/K328H/D330N, mutant D330A, mutant D330L, mutant D153H/D330A, mutant D153H/D330L, mutant K328H/D330A, mutant K328H/D330L, mutant D153H/K328H/D330A, mutant D153H/K328H/D330L, mutant Q329A, mutant D153H/Q329A, mutant K328H/Q329A and mutant D153H/K328H/Q329A.

7. The modified alkaline phosphatase of bacterial origin according to claim 1, wherein the bacterial alkaline phosphatase sequence is derived from *Escherichia coli* or from *Bacillus subtilis*.

8. The modified alkaline phosphatase of bacterial origin according to claim 1, wherein the bacterial alkaline phosphatase sequence contains, in addition to said at least one substitution, at least one additional amino acid inserted between amino acids +6 and +7 of the said bacterial alkaline phosphatase.

9. The modified alkaline phosphatase of bacterial origin according to claim 8, consisting of SEQ ID No. 1.

10. Diagnostic reagent, comprising an alkaline phosphatase according to any one of claim 1.

11. Modified alkaline phosphatase according to claim 1, identified as mutant D153H/K328H/Q329G/D330H.

12. A modified alkaline phosphatase of bacterial origin, comprising a wild-type bacterial alkaline phosphatase sequence in which at least one amino acid residue in position 330 is replaced by another amino acid residue, which modified alkaline phosphatase possesses a catalytic activity which is increased at pH 8 as compared with that of the wild type bacterial alkaline phosphatase and a thermal stability which is of the order of that of the said wild type alkaline phosphatase, said modified BAP being obtained by:

(i) preparing an inactive chimeric alkaline phosphatase, comprising the introduction, into the sequence encoding the wild-type BAP, of at least two codons encoding two amino acid residues from the active site of a mammalian alkaline phosphatase;

(ii) carrying out a random or site-directed mutagenesis on the gene which encodes the inactive chimeric alkaline phosphatase;

(iii) expressing the alkaline phosphatases obtained in (ii);

(iv) selecting bacterial clones which express an alkaline phosphatase whose enzyme activity has been restored; and (v) sequencing a mutated alkaline phosphatases thus obtained and selecting compatibility mutations to be introduced into a wild-type bacterial alkaline phosphatase.

13. The modified alkaline phosphatase according to claim 12, wherein the inactive chimeric alkaline phosphatase prepared in step (i) is identified as mutant D153H/K328H/Q329G/D330H.

14. The modified alkaline phosphatase according to claim 12, wherein said modified alkaline phosphatase possesses a catalytic activity which is increased by at least 189% at pH 8 as compared with that of the wild type bacterial alkaline phosphatase.

15. A modified alkaline phosphatase of bacterial origin, comprising a wild-type bacterial alkaline phosphatase (BAP) sequence in which one of the amino acid residues in position 329 or in position 330 is replaced by another amino acid residue, which modified alkaline phosphatase exhibits a catalytic activity and an affinity for a substrate which are increased as compared with activities of the corresponding wild-type BAP and a thermal stability which is of the order of that of said wild-type BAP.

16. The modified alkaline phosphatase of bacterial origin according to claim 14, wherein amino acid 330 is substituted and wherein the substitution at position 330 is the replacement by an amino acid residue, which modified alkaline phosphatase exhibits, at pH 8 an increase of 189% of its catalytic activity and a decrease of 251% of its $K_M$ as compared with that of the wild-type BAP and a thermal stability which is of the order of that of the said wild-type bacterial alkaline phosphatase.

17. The modified alkaline phosphatase of bacterial origin according to claim 15, wherein the substitution at position 330 is the replacement of an aspartic acid (Asp330 or D) by an asparagine.

18. The modified alkaline phosphatase of bacterial origin according to claim 5, wherein said modified BAP exhibits a catalytic activity which is increased at pH 10 by at least 317.5% as compared with that of the wild type BAP.

* * * * *